(12) United States Patent
Wright et al.

(10) Patent No.: US 11,911,461 B1
(45) Date of Patent: Feb. 27, 2024

(54) ADJUVANTED VACCINES CONTAINING MODIFIED S1 SPIKE PROTEIN OF SARS-COV-2 VARIANT C.1.2 FOR SUBCUTANEOUS ADMINISTRATION AND METHODS OF USE

(71) Applicant: D4 Labs, LLC, Pacific Grove, CA (US)

(72) Inventors: David Craig Wright, Pacific Grove, CA (US); Michael Bowe, Marina, CA (US); Emily Wright, Covina, CA (US); Peter Pushko, Frederick, MD (US)

(73) Assignee: D4 Labs, LLC, Pacific Grove, CA (US)

( * ) Notice: Subject to any disclaimer, the term of this patent is extended or adjusted under 35 U.S.C. 154(b) by 0 days.

(21) Appl. No.: 18/313,017

(22) Filed: May 5, 2023

(51) Int. Cl.
| | |
|---|---|
| *A61K 39/215* | (2006.01) |
| *A61K 39/00* | (2006.01) |
| *A61K 39/42* | (2006.01) |
| *A61P 31/14* | (2006.01) |
| *C07K 16/10* | (2006.01) |
| *A61P 37/04* | (2006.01) |

(52) U.S. Cl.
CPC ............ *A61K 39/215* (2013.01); *A61P 37/04* (2018.01); *A61K 2039/545* (2013.01); *A61K 2039/55555* (2013.01)

(58) Field of Classification Search
CPC ..... A61P 31/14; A61K 2039/53; A61K 39/12; A61K 39/215; C12N 2770/20021
See application file for complete search history.

(56) References Cited

U.S. PATENT DOCUMENTS

2022/0202930 A1   6/2022   Roth et al.

FOREIGN PATENT DOCUMENTS

| WO | WO 2022/076903 | 4/2022 |
|---|---|---|
| WO | WO 2022/110099 | 6/2022 |
| WO | WO 2022/226108 | 10/2022 |
| WO | WO 2023/279042 | 1/2023 |

OTHER PUBLICATIONS

Peng et al., "Advances in the design and development of SARS-COV-2 vaccines", 2021, 8(67):1-31.*
International Search Report for PCT/US2023/06667 dated Oct. 11, 202.
Tada et al., High-titer neutralization of Mu and C.1.2 SARS-COV-2 variants by vaccine-elicited 1-2, 5-6 antibodies of previously infected individuals. Cell Rep. Jan. 2022, vol. 38(2): 110237.
Arora et al., SARS-COV-2 variants C.1.2 and B.1.621 (Mu} partially evade neutralization by 1-9 antibodies elicited upon infection or vaccination. Cell Rep. May 2022, vol. 39(5): 110754.
Zhou et al., Role of COVID-19 Vaccines in SARS-COV-2 Variants. Front Immunol. 2022, vol. 1-9 13: 898192.
Magazine et al., Mutations and Evolution of the SARS-COV-2 Spike Protein. Viruses. 2022; Mar, vol. 14(3): 640.

* cited by examiner

*Primary Examiner* — Barry A Chestnut
(74) *Attorney, Agent, or Firm* — King & Spalding

(57) ABSTRACT

Disclosed herein are adjuvanted protein vaccines comprising: a SARS-CoV-2 variant C.1.2 modified S1 Spike protein sequence and a non-phospholipid liposome, wherein the protein is encapsulated within the non-phospholipid liposome. The adjuvanted protein vaccines are suitable for subcutaneous administration. Also disclosed herein are modified spike protein sequences containing SARS-CoV-2 variant C.1.2 modified S1 Spike proteins and methods of use of the vaccines and sequences.

16 Claims, 6 Drawing Sheets
Specification includes a Sequence Listing.

Figure 3

ADJUVANTED VACCINES CONTAINING MODIFIED S1 SPIKE PROTEIN OF SARS-COV-2 VARIANT C.1.2 FOR SUBCUTANEOUS ADMINISTRATION AND METHODS OF USE

FIELD OF THE INVENTION

Disclosed herein are features of adjuvanted SARS-CoV-2 S1 spike protein vaccines, and methods for preparing and using the same. The adjuvanted SARS-CoV-2 S1 spike protein vaccines are suitable for subcutaneous administration. Advantageously, the adjuvanted SARS-CoV-2 S1 spike protein vaccines generate an IgG antibody response with a single injection.

SEQUENCE LISTING

The instant application contains a Sequence Listing which has been submitted electronically in XML file format and is hereby incorporated by reference in its entirety. Said XML copy, created on May 5, 2023, is named 31579_105004_Sequence_Listing.xml and is 19,720 bytes in size.

BACKGROUND OF THE INVENTION

Vaccine development and usage over the years has significantly reduced the number of infections and diseases on a global basis. The need for vaccines persists, however, including for the treatment of emerging viral threats (e.g., SARS-CoV-2) and other viral agents.

Vaccines are based on the use of an intact viral or bacterial agent, either inactivated or live attenuated, cloned expressed proteins using molecular biology techniques, or mRNA. These vaccines frequently require two or more injections intramuscularly to develop a significant immune response. Additional boosters may be necessary to sustain immunity.

There remains a need for novel vaccine strategies, including novel adjuvanted protein vaccine strategies, particularly for emerging and recalcitrant bacterial, viral, and parasitic diseases. In particular, there remains a need for adjuvants that would generate an immune response with one or two vaccinations. Preferably, these adjuvants could be administered subcutaneously, not just intramuscularly, and could be stored at refrigerated temperatures.

SUMMARY OF THE INVENTION

Disclosed herein are features of adjuvanted SARS-CoV-2 spike protein vaccines, and methods for preparing and using the same. The vaccines are suitable for subcutaneous administration.

In a first aspect, an adjuvanted protein vaccine is disclosed, the vaccine comprising: a SARS-CoV-2 variant C.1.2 modified S1 Spike protein sequence and a non-phospholipid liposome, wherein the protein is encapsulated within the non-phospholipid liposome.

In a second aspect, a modified spike protein sequence is disclosed, the sequence comprising SARS-CoV-2 variant C.1.2 modified S1 Spike protein (amino acids 1-687) (SEQ. ID No. 3) or modified SARS-CoV-2 C.1.2 variant S1 spike protein with an additional amino acid His-tag (695 amino acids) (SEQ. ID No. 4).

In a third aspect, a method for generating an immune response in a subject, or preventing an infection in a subject, is disclosed, the method comprising subcutaneously administering an adjuvanted protein vaccine to a subject.

BRIEF DESCRIPTION OF THE FIGURES

FIG. 3. Depicts blot images for IgG antibodies directed against the full-length Spike protein of the SARS-CoV-2 Delta B.1.617.2 variant. The animals were subcutaneously immunized with a SVE52 nonphospholipid liposome containing vitamin E and a modified S1 sequence of the C.1.2 variant of SARS-CoV-2 (SEQ. ID No. 4). Animals were bled at days 0, 27, 49, and 122. Animals were immunized on days 1 and 28. The dilution of the sera was 1:500. High antibody responses by blot were noted in all five animals at days 49 and 122.

DETAILED DESCRIPTION OF THE INVENTION

Definitions

Figure 1:
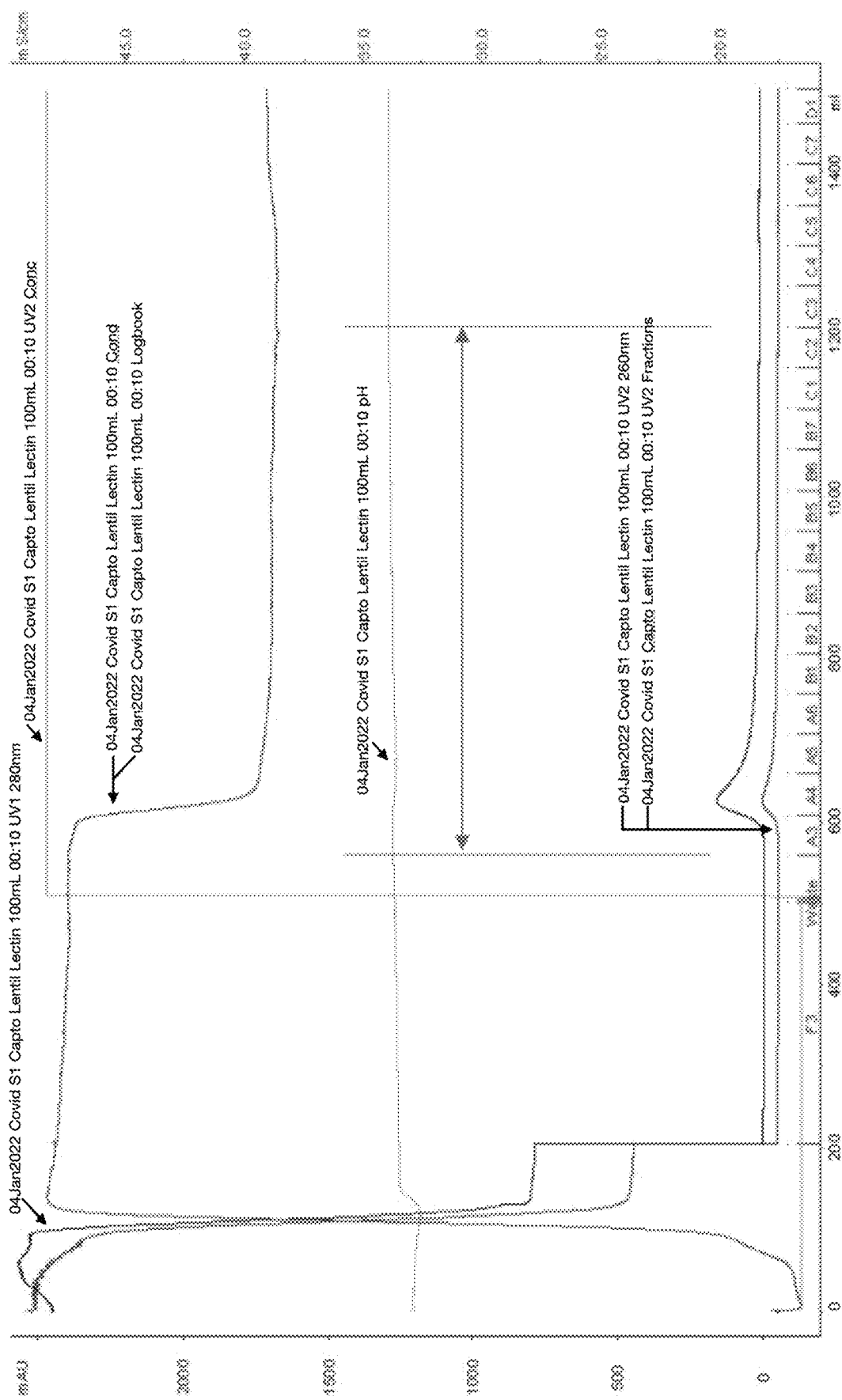
FIG. 1 depicts a chromatography graph of the resulting solution from purification of clarified cell culture supernatant containing the modified S1 subunit of the spike protein of C.1.2 (SEQ. ID No. 4) with affinity chromatography resin.

The term "about" as used herein refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

The term "adjuvant" as used herein refers to a substance whose admixture with an administered immunogenic determinant/antigen construct increases or otherwise modifies the immune response to said determinant. Immunological adjuvants function by attracting macrophages to the antigen and then to presenting said antigens to the regional lymph nodes and initiating an effective antigenic response. Conventional adjuvants can serve as vehicles for the antigen, and as nonspecific immunological stimulants. In one embodiment, the liposome (e.g., the paucilamellar liposome) serves as an adjuvant for the glycoprotein vaccine disclosed herein and in certain embodiments, incorporates Vitamin E.

The term "administering" as used herein means either directly administering a compound or composition of the present invention. Any route of administration, such as topical, subcutaneous, peritoneal, intravenous, intraarterial, inhalation, vaginal, rectal, nasal, buccal, introduction into the cerebrospinal fluid, or instillation into body compartments can be used. The terms and phrases "administering" and "administration of," when used in connection with a compound or pharmaceutical composition (and grammatical equivalents) refer both to direct administration, which may be administration to a patient by a medical professional or by self-administration by the patient, and/or to indirect administration, which may be the act of prescribing a drug.

The term "affinity" as used herein refers to the equilibrium constant for the reversible binding of two agents and is expressed as a dissociation constant (KD).

The term "amino acid" or "amino acids" as used herein is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids (stereoisomers). Abbreviations for amino acids are well understood in the art.

The term "amphiphilic" as used herein means exhibiting characteristics of hydrophilicity and lipophilicity. Common amphiphilic substances are soaps, detergents and lipoproteins. Other examples of amphiphilic compounds are: saponins, phospholipids, glycolipids, polysorbates.

The term "antigen" as used herein refers to a molecule with one or more epitopes that stimulate a host's immune system to make a secretory, humoral and/or cellular antigen-specific response, or to a DNA molecule that is capable of producing such an antigen in a vertebrate. The term is also used interchangeably with "immunogen." For example, a specific antigen can be complete protein, portions of a protein, peptides, fusion proteins, glycosylated proteins and combinations thereof.

The term "binding" as used herein refers to direct association between two molecules, due to, for example, covalent, electrostatic, hydrophobic, and ionic and/or hydrogen-bond interactions, including interactions such as salt bridges and water bridges. "Specific binding" refers to binding with an affinity of at least about 10-7 M or greater.

The term "boost" as used herein refers to the administration of an additional dose of an immunizing agent, such as a vaccine, administered at a time after the initial dose to sustain the immune response elicited by the previous dose of the same agent.

The term "C.1.2 variant" as used herein refers to the unique SARS-CoV-2 variant that was not a part of the Delta, Omicron, nor any other family of variants.

The term "carrier" as used herein includes any solvent(s), dispersion medium, coating(s), diluent(s), buffer(s), isotonic agent(s), solution(s), suspension(s), colloid(s), inert (s), or such like, or a combination thereof that is pharmaceutically acceptable for administration to the relevant animal or acceptable for a therapeutic or diagnostic purpose, as applicable.

The terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "conservative amino acid substitution" as used herein refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine-glycine, and asparagine-glutamine.

The term "coronavirus" as used herein refers to positive strand RNA viruses with the largest viral genome among the RNA viruses (27-33 kb). The virus particles are enveloped and carry extended spike proteins on the membrane surface, providing the typical crown-like structure. The coronaviruses share a conserved organization of their (positive strand) RNA genome. The 5' two-thirds of the genome contains the large 1a and 1b ORFs, encoding the proteins necessary for RNA replication (the nonstructural proteins), whereas the 3' one-third contains the genes coding for the structural proteins: haemagglutinin esterase protein (only for group Ha), spike protein, envelope protein, membrane protein and nucleocapsid protein. The accessory protein genes are interspersed between the structural protein genes and differ in number and position for the various coronavirus. Several coronavirus genera and subgenera are recognized (https://talk.ictvonline.org/ictv-reports/). Among them, alpha- and betacoronaviruses infect mammals, gammacoronaviruses infect avian species, and deltacoronaviruses infect both mammalian and avian species. The coronavirus may be, for example, 229E, SARS, MERS, SARS-CoV-1 (OC43), and SARS-CoV-2. The coronavirus spike protein includes three segments: a large ectodomain, a single-pass transmembrane anchor, and a short intracellular tail The ectodomain consists of a receptor-binding subunit S1 and a membrane-fusion subunit S2. The S1 and S2 domains may be separated by a cleavage site that is recognized by furin-like proteases during S protein biogenesis in the infected cell. The spike protein binds to a receptor on the host cell surface through the S1 subunit and then fuses viral and host membranes through its S2 subunit. The spike protein exists in two structurally distinct conformations, pre-fusion and post-fusion. The S1 subunit of the betacoronavirus spike proteins displays a multidomain architecture and is structurally organized in four distinct domains A-D of which domains A and B may serve as a Receptor Binding Domain (RBD).

The term "cross-reacts" as used herein refers to the reaction between an antigen and an antibody that was generated against a different but similar antigen.

The term "encapsulate" as used herein refers to the lipid vesicle forming an impediment to free diffusion into solution by an association with or around an agent of interest, e.g., a lipid vesicle may encapsulate an agent within a lipid layer or within an aqueous compartment inside or between lipid layers.

The term "identical" or percent "identity," in the context of two or more nucleic acids or polypeptide sequences, may refer to two or more sequences or subsequences that are the same or have a specified percentage of amino acid residues or nucleotides that are the same. In some cases, 2 or more sequences may be homologous (homologs) if they share at least 20%, 25%, 30%. 35%, 40%, 45% 50%, 55%, 60%, 65%, 70%, 75%, 80%, 85%, 90%, 91%, 92%, 93%, 94%, 95%, 96%, 97%, 98%, 99%, or higher identity to a reference sequence when compared and aligned for maximum correspondence over a comparison window, or designated region as measured using one of the following sequence comparison algorithms or by manual alignment and visual inspection.

The term "incorporating" or "incorporated" as used herein with reference to a liposome means encapsulated/encapsulating into the cavity of the liposome, within the potential double layer of the liposome, or as part of the membrane layer of the liposome.

The term "immune response" as used herein refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (e.g., prevents infection or prevents the development of disease associated with infection). Methods of measuring immune responses are well known in the art and include, for example, by measuring proliferation and/or activity of lymphocytes (such as B or T cells), secretion of cytokines or chemokines, inflammation, antibody production and the like. "Enhancing an immune response" refers to co-administration of an adjuvant and at least one peptide, wherein the adjuvant increases the desired immune response to the at least one peptide compared to administration of the at least one peptide in the absence of the adjuvant.

The term "immunogenic composition" as used herein are those which result in specific antibody production or in cellular immunity when injected into a subject. In certain embodiments, the vaccine disclosed elicits a neutralizing antibody response.

The term "immunogenic variants" as used herein, refers to a variant that that is predicted to be immunogenic.

The term "liposome" as used herein refers to a vesicle made of concentric bilayers of lipids and more particularly, non-phospholipids or lipids which do not comprise phosphates groups. The liposome can be formed of the same lipid or different lipids. These lipids can have an anionic, cationic or zwitterionic hydrophilic head group. The size of a liposome may vary but is generally from about 10 to about 3000 nm. In certain embodiments, the liposome has an aqueous core, while in other embodiments, the liposome has an oil and water-filled core. The term "empty liposome" as used herein refers to a liposome not incorporating any peptide or other antigen within the liposome core.

The term "multilamellar" as used here refers to a vesicle containing more than one lipid bilayers.

The term "non-ionic surfactant" as used herein refers to a class of surfactants which have no charge groups in their hydrophilic heads. In solutions, nonionic surfactants form structures in which hydrophilic heads are opposite to aqueous solutions and hydrophilic tails are opposite to organic solutions. Representative, non-limiting non-ionic surfactants include alkyl esters, alkyl amides, alkyl ethers and esters of fatty acids.

The term "paucilamellar" as used herein refers to a vesicle having 2-10 lipid bilayers. In certain embodiments disclosed herein the vesicle that contains five or more polypeptides is paucilamellar.

The term "pharmaceutical composition" refers to a mixture of one or more chemicals, or pharmaceutically acceptable salts thereof, with a suitable carrier, for administration to a mammal as a medicine.

The term "phospholipid" as used herein refers to any of a group of lipids whose molecule has a hydrophilic "head" containing a phosphate group, and two hydrophobic "tails" derived from fatty acids, joined by a glycerol molecule. The phosphate group can be modified with simple organic molecules such as choline, ethanolamine or serine. In certain embodiments herein, the liposome does not contain phospholipids.

The term "prophylactic" as used herein with reference to an immunogenic composition (e.g., a vaccine) that is administered to a subject who does not exhibit signs of a disease.

The term "protein" as used herein refers to a sequence of amino acid residues between 600 and 1,300 amino acids in length.

The term "recombinant" as used herein refers to intended to refer to proteins that are designed, engineered, prepared, expressed, created, or isolated by recombinant means, such as proteins expressed using a recombinant expression vector transfected into a host cell, proteins isolated from a recombinant, combinatorial proteins library, or proteins prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. In some embodiments, one or more such selected sequence elements results from the combination of multiple (e.g., two or more) known sequence elements that are not naturally present in the same protein.

The term "spike protein", as used herein, refers to a type I transmembrane glycoprotein that is characteristic of coronaviruses. Most spike proteins contain a leader, an ectodomain, a transmembrane domain and an intracellular tail.

The term "stability" as used herein refers to product stability for vaccine products manufactured by D4 Labs. A product is determined stable if the change in size shows a less than 10% increase in size when measured on a Beckman Coulter Laser Sizer LS 13 320 XR.

The term "subject in need thereof" as used herein refers to a living organism suffering from or prone to a disease or condition that can be treated by using the methods provided herein. The term does not necessarily indicate that the subject has been diagnosed with a particular disease or disorder, but typically refers to an individual under medical supervision. Non-limiting examples include humans, other mammals, bovines, rats, mice, dogs, monkeys, goat, sheep, cows, deer, and other non-mammalian animals. In embodiments, a patient is human.

The term "therapeutic activity" or "activity" may refer to an activity whose effect is consistent with a desirable therapeutic outcome in humans, or to desired effects in non-human mammals or in other species or organisms. Therapeutic activity may be measured in vivo or in vitro. For example, a desirable effect may be assayed in cell culture.

The terms "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance.

The term "vaccine" as used herein, refers to any type of biological preparation contributing to or soliciting active immune responses against a particular disease or pathogen. Such biological preparation can include, but is not limited to, an antigen derived from a disease-causing agent or a portion of an antigen derived from a disease-causing agent.

The term "vaccination" or "vaccinate" refers to the administration of a composition intended to generate an immune response, for example to a disease-causing agent. Vaccination can be administered before, during, and/or after exposure to a disease-causing agent, and/or to the development of one or more symptoms, and in some embodiments, before, during, and/or shortly after exposure to the agent. In some embodiments, vaccination includes multiple administrations, appropriately spaced in time, of a vaccinating composition.

The term "vaccine efficacy" or "VE" as used herein measure the proportionate reduction in cases among vaccinated persons. It is measured by calculating the risk of disease among vaccinated and unvaccinated persons and determining the percentage reduction in risk of disease among vaccinated persons relative to unvaccinated persons. The greater the percentage reduction of illness in the vaccinated group, the greater the vaccine efficacy.

The term "variant" as used refers to a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence. A "variant" of a protein may have at least 70%, 75%, 80%, 85%, 90%, 95%, 98% or 99% amino acid identity over a stretch of 10, 20, 30, 50, 75 or 100 amino acids of such protein. Variants of the proteins as defined herein, which may be encoded by a nucleic acid molecule, may also comprise those sequences, wherein nucleotides of the encoding nucleic acid sequence are exchanged according to the degeneration of the genetic code, without leading to an alteration of the respective amino acid sequence of the protein, i.e., the amino acid sequence or at least part thereof may not differ from the original sequence in one or more mutation(s) within the above meaning.

The term "vesicle" as used herein refers to a structure comprising liquid or cytoplasm enclosed by a lipid bilayer. The interior of the vesicle is typically an aqueous environment but can also be an oily environment, and it may comprise an agent such as but not limited to a prophylactic, therapeutic or diagnostic agent.

Disclosed herein are immunogenic compositions, such as adjuvanted vaccine, which comprise a lipid vesicle, such as a non-phospholipid liposome, and a SARS-CoV-2 variant C.1.2 modified S1 Spike protein, wherein the protein is encapsulated within the lipid vesicle.

A SARS-CoV-2 variant C.1.2 modified S1 Spike protein sequence is also disclosed.

Methods of use of the immunogenic compositions, liposomes and sequences are also disclosed herein.

Advantageously, the immunogenic compositions or vaccines disclosed herein can be administered subcutaneously. In certain embodiments, the vaccines require a single vaccination with one boost for efficacy. In certain embodiments, the vaccines can be stored at refrigerated temperatures.

Compositions

The present disclosure provides immunogenic (or pharmaceutical) compositions, such as vaccines) comprising a SARS-CoV-2 variant C.1.2 modified S1 Spike protein sequence and a lipid vesicle, such as a liposome. In one embodiment, the composition is an adjuvanted protein vaccine comprising one or more proteins and a lipid vesicle, such as a liposome. In certain embodiments, one or more proteins is encapsulated within a liposome. These compositions are suitable for use, for example, in generating an immune response as described further herein. In certain embodiments, the vaccine facilitates generation of IgG antibodies to spike proteins from multiple SARS-CoV-2 variants.

In one embodiment, the composition is an adjuvanted SARS-CoV-2 variant C.1.2 modified S1 Spike protein sequence vaccine.

As described herein, nonphospholipid adjuvants can be used to encapsulate a modified S1 Spike protein sequence of a C.1.2 SARS-CoV-2 variant. The total length of amino acids is 682 from the modified S1 protein (Seq. ID No. 3). Adding a 13 amino acid length His-tag creates a 695 amino acid construct (SEQ. ID No. 4). This construct includes N3 and N5 neutralizing bonding sites, the receptor binding domain and the receptor binding motif of SARS-CoV-2, and multiple T cell epitopes. Amino acids 683-1,270 were deleted to determine if the immunogenic compositions could generate high-titered IgG antibody responses to native Spike proteins of SARS-CoV-2. In deleting amino acids after position 683 of the Spike protein, five sequences containing peptides with homology to seven human proteins have been deleted.

Subcutaneous administration of two doses of this protein liposomal vaccine at days 1 and 28 results in immunogenicity that persists for greater than 122 days in a Syrian golden hamster model. Antisera from these animals recognized the following SARS-CoV-2 variant Spike proteins: Hu-1, Delta, and Omicron BA.1.

Proteins

The compositions (e.g., vaccines) disclosed herein include at least one modified S1 sequence of the SARS-CoV-2 spike protein, (i.e., a SARS-CoV-2 variant C.1.2 modified S1 Spike protein sequence).

The compositions can comprise one or more additional proteins. In certain embodiments, the compositions could contain a combination of proteins. In certain embodiments, the composition or vaccine comprises at least one, at least two, at least three, or at least four, or at least five or more proteins.

In certain embodiments, the immunogenic compositions could contain a combination of modified S1 sequences of the spike protein, or a construct containing two or more S1 spike protein sequences in the same construct.

In certain embodiments, the immunogenic composition cross-reacts with full-length SARS-CoV-2 spike proteins. In one embodiment, the protein is a modified S1 sequence of the spike protein, administered subcutaneously, that generates IgG antibody responses for 122 days after two injections of the adjuvanted protein vaccine.

In one embodiment, the protein is a modified S1 sequence of the C.1.2 SARS-CoV-2 variant. In one embodiment, the sequence of the modified S1 subunit of the Spike protein from the C.1.2 variant of SARS-CoV-2 is SEQ. ID. No. 4.

In certain embodiments, the protein is a SARS-CoV-2 spike protein, such as the spike protein of the SARS-CoV-2 C.1.2 variant, or a modified version thereof. In certain embodiments, the protein is a modified S1 sequence of a SARS-CoV-2 C.1.2 variant with an additional amino acid His-tag, such SEQ. ID No. 4.

In certain embodiments, the vaccine contains at least one protein derived from SEQ ID No.:1, which is the SARS-CoV-2 C.1.2 Spike protein sequence from Accession #ULM22659.

In one embodiment, the one or more additional proteins are selected from:
  (i) a modified S1 Spike protein that generates IgG antibody responses for 122 days after two injections of the adjuvanted protein vaccine, by subcutaneous or intramuscular routes;
  (ii) a modified spike protein sequence of a coronavirus;
  (iii) a protein sequence from a coronavirus; and
  (iv) a protein from an infectious agent that generates IgG antibody responses to proteins after one or two subcutaneous or intramuscular injections.

In one embodiment, the protein is a protein sequence from a coronavirus.

In one embodiment, the protein is a protein from an infectious agent, for example an infectious agent that generates IgG antibody responses to proteins after one or two subcutaneous or intramuscular injections.

In one embodiment, the viral protein is derived from a DNA virus selected from the group consisting of adenovirus, papillomavirus, parvovirus, herpes simplex virus, varicella-zoster virus, cytomegalovirus, Epstein-Barr virus, smallpox virus, vaccinia virus, and hepatitis B virus.

In another embodiment the viral protein is derived from an RNA virus selected from the group consisting of tavirus, norovirus, enterovirus, hepatovirus, rubella virus, influenza viruses (A, B, and C), measles virus, mumps virus, hepatitis C virus, yellow fever virus, hantavirus, Zika virus, California encephalitis virus, rabies virus, Ebola virus, and HIV.

In one embodiment, the viral protein is from a coronavirus. The coronavirus can be any coronavirus currently known, or later discovered. In certain embodiments, the coronavirus is zoogenic.

In a particular embodiment, the viral protein is from SARS-CoV-2 or a variant thereof. SARS-CoV-2 can cause severe respiratory illness and significant mortality among those over 65 years old or with chronic conditions.

In one embodiment, the viral protein is derived from the spike (S) protein of the coronavirus. Other relevant proteins like envelope (E), membrane (M), nucleocapsid (N) protein of the coronavirus or a combination thereof could occur.

In a particular embodiment, one protein is produced from a known viral protein sequence, and more particularly the spike protein of SARS-CoV-2.

In one embodiment, all proteins are glycoproteins.

Amino acids 683-1,270 were deleted to determine if the immunogenic compositions could generate high-titered IgG antibody responses to native Spike proteins of SARS-CoV-2. In deleting amino acids after position 683 of the Spike protein, five sequences containing peptides with homology to seven human proteins have been deleted.

One sequence in the spike protein VMVTIMLCCMTSCCSCLKGC (SEQ. ID. No. 5) at amino acids 1228-1247 has sequence homology to CCMSSCC (SEQ. ID. No. 6) which is found in keratin associated protein4-7 (KRTAP4-7) in human skin. The same sequence in the spike protein VMVTIMLCCMTSCCSCLKGC (SEQ. ID. No. 5) at amino acids 1228-1247 has sequence homology to CKTSCCSC (SEQ. ID. No. 7) in Metallothionein 1E (MT1E) found in human liver and many other tissues. Accession number AA032957.

A second sequence in the spike protein LNEVAKNLNESLIDLQELGK (SEQ. ID. No. 8) at amino acids 1186-1205 has sequence homology to KNMEEGLITLQEL (SEQ. ID. No. 9) which is found in human Coiled-coil domain-containing protein 175 isoform X8 which is found in human brain, pituitary gland, and testis. Accession number XP_011535432.

A third sequence in the spike protein KEELDKYFKNHTSPDVDLGD (SEQ. ID. No. 10) at amino acids 1149-1168 has sequence homology to EILDKYFKN (SEQ. ID. No. 11) which is found in Follistatin-related protein 1 isoform X1 in human placenta. Accession number XP_024309095.

A fourth sequence in the spike protein QQLIRAAEIRASANLAATKM (SEQ. ID. No. 12) found at amino acids 1010-1029 has sequence homology to QQLGIAEDLKDRAAEGRASSNL (SEQ. ID. No. 13) which is found in human Tetratricopeptide repeat protein 28 isoform X8 found ubiquitously in human tissue. Accession number XP_011528323.

A fifth sequence in the spike protein TLVKQLSSNFGAISSVLNDI (SEQ. ID. No. 14) at amino acids 961-980 has sequence homology to LVKNIQLEDGKMILASNFFKGAASSVL (SEQ. ID. No. 15) which is found in human ALDH1L1 protein found ubiquitously in human tissue. Accession number AAH27241. The same sequence in the spike protein TLVKQLSSNFGAISSVLNDI (SEQ. ID. No. 14) at amino acids 961-980 has sequence homology to FGAISSVLNDI (SEQ. ID. No. 16) in Attractin-like protein 1 which is found in human brain. Accession number XP_016871528. The same sequence in the spike protein TLVKQLSSNFGAISSVLNDI (SEQ. ID. No. 14) at amino acids 961-980 has sequence homology to AIASALIDI (SEQ. ID. No. 17) in Attractin-like protein 1 which is found in human brain. Accession number XP_016871528.

TABLE 1

| Spike Sequence Deleted | Amino Acid | Human Protein | Accession Number NCBI | Homologous Region within Human Protein |
|---|---|---|---|---|
| VMVTIMLCCMTSCCSCLKGC (SEQ. ID. No. 5) | 1228-1247 | Keratin associated protein 4-7 (KRTAP P4-7) | NP_149050 | CCMSSCC (SEQ. ID. No. 6) |
| VMVTIMLCCMTSCCSCLKGC (SEQ. ID. No. 5) | 1228-1247 | Metallothionein 1E (MT1E) | AA032957 | CKTSCCSC (SEQ. ID. No. 7) |
| LNEVAKNLNESLIDLQELGK (SEQ. ID. No. 8) | 1186-1205 | Coiled-coil domain-containing protein 175 isoform X8 | XP_011535432 | KNMEEGLITLQEL (SEQ. ID. No. 9) |
| KEELDKYFKNHTSPDVDLGD (SEQ. ID. No. 10) | 1149-1168 | Follistatin-related protein isoform X1 | XP_024309095 | EILDKYFKN (SEQ. ID. No. 11) |
| KEELDKYFKNHTSPDVDLGD (SEQ. ID. No. 10) | 1149-1168 | Follistatin-related protein | XP_024309095 | EILDKYFKN (SEQ. ID. No. 11) |
| QQLIRAAEIRASANLAATKM (SEQ. ID. No. 12) | 1010-1029 | Tetratricopeptide repeat protein 28 | XP_011528323 | QQLGIAEDLKDRAAEGRASSNL (SEQ. ID. No. 13) |
| QQLIRAAEIRASANLAATKM (SEQ. ID. No. 12) | 1010-1029 | Tetratricopeptide repeat protein 28 isoform X8 | XP_011528323 | QQLGIAEDLKDRAAEGRASSNL (SEQ. ID. No. 13) |
| TLVKQLSSNFGAISSVLNDI (SEQ. ID. No. 14) | 961-980 | Attractin-like protein 1 | XP_016871528 | FGAISSVLNDI (SEQ. ID. No. 16) |
| TLVKQLSSNFGAISSVLNDI (SEQ. ID. No. 14) | 961-980 | Attractin-like protein 1 | XP_016871528 | AIASALIDI (SEQ. ID. No. 17) |
| TLVKQLSSNFGAISSVLNDI (SEQ. ID. No. 14) | 961-980 | ALDH1L1 protein | AAH27241 | LVKNIQLEDGKMILASNFFKGAASSVL (SEQ. ID. No. 15) |

The mutation chart for the SARS-CoV-2 variants Delta, Omicron BA.1, C.1.2, and the exemplary S1 construct based on the C.1.2 mutations is shown in Table 2. C.1.2 contains many of the mutations that had caused worldwide infections and death.

TABLE 2

| Delta | BA.1 | C.1.2 | S1 Construct |
|---|---|---|---|
| T19R | A67V | P9L | P9L |
| E156G | del69/70 | C136F | P25L |
| del157/158 | T95I | del144Y | C136F |
| L452R | G142D | R190S | del 144Y |
| T478K | del143/145 | D215G | W152K |
| D614G | N211I | del243-244AL | R190S |
| P681R | del212/212 | Y449H | D215G |
| D950N | G339D | E484K | del243-244AL |
|  | S371L | N501Y | F275Y |
|  | S373P | D614G | L276I |
|  | S375F | H655Y | R346K |
|  | S477N | N679K | N440K |
|  | T478K | T716I | Y449H |
|  | E484A | T859N | E484K |
|  | Q493R |  | N501Y |
|  | G496S |  | D614G |
|  | Q498R |  | H655Y |
|  | N501Y |  | N679K |
|  | Y505H |  | P681H |
|  | T547K |  |  |
|  | D614G |  |  |
|  | H655Y |  |  |
|  | N679K |  |  |
|  | P681H |  |  |
|  | N764K |  |  |
|  | D796Y |  |  |

Lipid Vesicle

The one or more proteins can be provided with, or encapsulated within, a lipid vesicle, such as a liposome.

Lipid vesicles are substantially spherical structures made of amphiphiles, e.g., surfactants or phospholipids. The lipids of these spherical vesicles are generally organized in the form of lipid bilayers, e.g., multiple onion-like shells of lipid bilayers which encompass an aqueous volume between the bilayers. Certain types of lipid vesicles have an unstructured central cavity which can be used to encapsulate and transport a variety of materials. The lipid vesicle may be charged or neutral.

The lipid vesicle may be any suitable lipid vesicle such as a liposome, e.g., a non-phospholipid (or a non-phospholipid-based) liposome. The liposome may comprise an adjuvanting oil. The lipid vesicle may be a unilamellar or multilamellar vesicle. Multilamellar vesicles are concentric circles constructed by at least 2 bilayer vesicles or a large vesicle embodying one or more small vesicles.

Liposome properties differ and may be selected on the basis of lipid composition, surface charge, size, and the method of preparation. Typically, liposomes can be divided into three categories based on their overall size and the nature of the lamellar structure. In one embodiment, the liposome is a small unilamellar vesicle (SUV) between about 20 and about 100 nm, a large unilamellar vesicle (LUV) greater than about 100 nm, a giant unilamellar vesicle (GULV) greater than about 100 nm, an oligolamellar vesicle (OLV) between about 100 and about 1000 nm or a multilamellar large vesicle (MLV) greater than about 500 nm.

In one embodiment, the lipid vesicle is a liposome formed from one or more non-phospholipid amphiphiles, such as one or more non-ionic surfactants and optionally, a membrane stabilizer such as cholesterol. Membrane stabilizers may be included to improve one or more properties of the liposome.

In certain embodiments, the lipid vesicle is a non-phospholipid-based liposome containing vitamin E. The lipid vesicle may be a unilamellar or multilamellar vesicle. Multilamellar vesicles are concentric circles constructed by at least 2 bilayer vesicles or a large vesicle embodying one or more small vesicles.

In one embodiment, the non-phospholipid liposome comprises: one or more polyoxyethylene fatty acid ethers, one or more membrane stabilizing agents, one or more negative charge producing agents, and Vitamin E. The non-phospholipid liposome may further comprise water, e.g., sterile water.

In one embodiment, the non-phospholipid liposome comprises one or more polyoxyethylene fatty acid ethers. In one embodiment, the one or more polyoxyethylene fatty acid ethers comprises polyoxyethylene 2-stearyl ether. In one embodiment, the one or more polyoxyethylene fatty acid ethers comprises polyoxyethylene 2-cetyl ether.

In one embodiment, the non-phospholipid liposome comprises one or more membrane stabilizing agents, for example a sterol. In one embodiment, the sterol is cholesterol. In one embodiment, the sterol is cholesterol derivative.

In one embodiment, the non-phospholipid liposome comprises one or more negative charge producing agents, for example oleic acid.

In one embodiment, the liposome suitable for use in a protein vaccine.

In one embodiment, the protein vaccine is suitable for subcutaneous or intramuscular administration.

In one embodiment, the lipid vesicle is a non-phospholipid-based liposome comprising, or consisting essentially of, polyoxyethelene 2-cetyl ether, cholesterol, oleic acid, vitamin E, and sterile water, and the non-phospholipid-based liposome contains the protein.

In one embodiment, the lipid vesicle is a non-phospholipid-based liposome comprising, or consisting essentially of, polyoxyethylene 2-stearyl ether, cholesterol, oleic acid, vitamin E, and sterile water, and the non-phospholipid-based liposome contains the protein.

In certain embodiments, the lipid vesicle or liposome comprises one or more polyoxyethylene fatty acid ether compound (e.g., polyoxyethelene 2-stearyl ether or polyoxyethelene 2-cetyl ether), one or more sterol compounds (e.g., a membrane stabilizer such as cholesterol), one or more negative-charge-producing agent (e.g., oleic acid), and Vitamin E. The lipid vesicle or liposome may further comprise any lipid soluble or water-soluble materials to be incorporated into the vesicles.

In certain embodiments, the lipid vesicle or liposome does not comprise phospholipids. In certain embodiments, the lipid vesicle or liposome does not comprise squalene.

In certain embodiments, the lipid vesicle or liposome comprises Vitamin E.

In certain embodiments, the lipid vesicle or liposome comprises sterile water.

In certain embodiments, the lipid vesicle or liposome contains or encompasses one or more proteins.

Liposome properties may differ and can be selected on the on the basis of lipid composition, surface charge, size, and the method of preparation.

In one embodiment, the lipid vesicle is a liposome selected from a small unilamellar vesicle (SUV) (10-100 nm), a large unilamellar vesicle (LUV) (100-3000 nm) and multilamellar vesicle (MLV). In certain embodiments, liposome is a vesicle comprising between 2 and about 10 layers. The 2 to 10 peripheral bilayers encapsulate an aqueous volume which is interspersed between the lipid bilayers and may also be encapsulated in the amorphous central cavity. Alternatively, the amorphous central cavity may be substantially filled with a water immiscible material, such as an oil or wax. The paucilamellar vesicles containing such amphiphiles provide a high carrying capacity for water-soluble and water immiscible substances. The high capacity for water immiscible substances represents a unique advantage over classical phospholipid multilamellar liposomes.

The lipid vesicle contains a central cavity, carrying either water soluble materials or a water-immiscible oily solution, which can be used to encapsulate the antigen or protein. The water-immiscible oily solution is made of materials which are both water immiscible and immiscible in the lipids used to form the bilayers. In certain embodiments, the water immiscible oily material found in the amorphous central cavity comprises Vitamin E.

In certain embodiments, oleic acid can insert in the membrane allowing negatively charged structures to be produced.

Carriers and Modes of Administration

In certain embodiments, the immunogenic composition (e.g., vaccine) includes a pharmaceutically acceptable carrier. The pharmaceutically acceptable carrier may be formulated for administration to a human subject or animal.

In some embodiments, the pharmaceutically acceptable carrier includes diluents and adjuvants. Diluents include, for example, water or saline.

Compositions may be prepared as injectables, either as liquid solutions or suspensions. The composition may be prepared for nasal administration, e.g. as drops. Compositions may be presented in vials, or they may be presented in ready-filled syringes. The syringes may be supplied with or without needles. A syringe will include a single dose of the composition, whereas a vial may include a single dose or multiple doses.

The composition may be packaged in unit dose form or in multiple dose form.

Methods of Use

The compositions and vaccines described herein are useful, for example, for generating an immune response. Generally, the method includes contacting the cell with an effective amount of the compositions or vaccines described herein.

In some embodiments, methods of inducing an immune response are used for vaccination. The methods involve administering a prophylactically effective amount of the immunogenic composition as described herein to prevent an infection by, or an amount sufficient to reduce the biological activity of, an infectious agent such as a virus (e.g., a coronavirus).

In one embodiment, a method for generating an immune response in a subject comprises administering an adjuvanted protein vaccine to the subject.

In one embodiment, a method for preventing an infection in a subject comprises administering an adjuvanted protein vaccine to the subject.

In one embodiment, the method comprises administering an adjuvanted protein vaccine is subcutaneously or intramuscularly. In one embodiment, the method generates an IgG immune response. In one embodiment, the method increases the immune response to SARS-CoV-2 spike protein. In one embodiment, the method comprises administering the adjuvanted protein vaccine in one or more doses.

In certain embodiments, the vaccine is a prophylactic vaccine, i.e., confers immunity to a subject who is not infected. According to this embodiment, the method comprising administering the vaccine to a subject in need thereof. In certain embodiments, administration is subcutaneous.

For example, and without limitation, the one or more subsequent exposures occurring administration may result in reduced viral titers, reduced amount and/or severity of symptoms, shortened duration of symptoms, and/or reduced need for treatment medications and/or clinician oversight, as compared to a control.

In certain embodiments, the immunogenic composition (e.g., vaccine) is administered to a subject as a single dose followed by a second dose later. In one embodiment the immunogenic composition (e.g., vaccine) and/or booster administrations may be repeated and such administrations may be separated by at least 28 days after the initial dose.

In one embodiment, the vaccine disclosed herein is administered as a booster to one or more vaccines known in the art. In a particular embodiment, the vaccine disclosed herein is administered as a booster to an mRNA vaccine or an adenoviral vaccine. In a particular embodiment, the vaccine disclosed herein is a booster to a SARS-CoV-2 vaccine selected from the Pfizer-BioNTech COVID-19 vaccine, the Moderna COVID-19 vaccine, the Janssen COVID-19 vaccine, or the Novavax COVID-19 vaccine.

Administration may be by any suitable mode known in the art. In a particular embodiment, administration is subcutaneous.

The useful dosage administered may vary. In one embodiment, the suitable dose is about 7 to about 10 µg of antigen per animal.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least about 3 weeks apart, more particularly about 4 weeks apart.

The subject may be an animal, preferably a vertebrate, more preferably a mammal. Exemplary subject includes, e.g., a human, a cow, a pig, a chicken, a cat or a dog, as the infectious agents covered herein may be problematic across a wide range of species. Where the vaccine is for prophylactic use, the human is preferably a teenager, or an adult.

Methods of Preparation

The immunogenic compositions (e.g., vaccines) disclosed herein may be prepared by any suitable method.

The protein of the immunogenic composition disclosed herein can be made in any suitable way. Proteins are chemically synthesized.

Once a lipophilic phase is made, it is blended with an aqueous phase (e.g., water, saline, or any other aqueous solution which will be used to hydrate the lipids), which contain protein antigens, under shear mixing conditions to form the adjuvanted protein vaccine.

In one embodiment, the lipid vesicle is prepared utilizing high sheer technology.

In one embodiment, the lipid vesicle (e.g., non-phospholipid-based liposome) is loaded by direct entrapment.

The final concentration of peptide in the adjuvanted vaccine may vary. In one embodiment, the final concentration is in the range of about 5 to about 12, or about 7 to about 10, µg of protein (or antigen) in each vaccine dose.

In certain embodiments, the vaccine is manufactured using cell culture technique, such as that which is used commercially to produce a baculovirus-expressed SARS-CoV-2 spike protein based on the original Wuhan Hu-1 sequence of SARS-CoV-2 from December 2019.

The following Examples are intended to be non-limiting.

EXAMPLES

Example 1: Preparation of an Exemplary Protein

A. Expression of Genes of Interest (GOD, Modified S1 Sequence of C.1.2 (SEQ. ID No. 4) in Baculovirus Expression Vector System 1. Synthesis and Cloning of GOI into Transfer Vector.

The GOI sequence (SEQ. ID No. 4) was based on the modified S1 sequence of the spike protein of C.1.2 (SEQ. ID No. 3) provided D4 Labs LLC. The gene was designed by optimization of nucleotide codon bias for high-level expression in insect cells. The gene was biochemically synthesized de novo and cloned into pFastBac1-baculovirus transfer vector. The GOI sequence and adjacent vector sequences were confirmed by DNA sequencing.

2. Cloning or GOI from Transfer Vector into Recombinant Baculovirus.

Bac-to-Bac system (ThermoFisher Invitrogen) was used for Cloning or GOI from transfer vector into recombinant baculovirus. Recombinant bacmids were produced by site-specific homologous recombination following transformation of bacmid transfer pFastBac1-GOI plasmids containing GOI into *E. coli* DH10Bac competent cells, which contained the AcMNPV baculovirus genome (Invitrogen). The recombinant bacmid DNA was transfected into the Sf9 insect cells seeded in 6-well plates at 0.5×106 cells/ml using Fugene 6 reagent (Invitrogen protocol). At 72 h post-transfection, cells were harvested for recovery in the culture medium of recombinant baculoviruses containing GOI.

3. Cell Culture and Baculovirus Infections.

*Spodoptera frugiperda* Sf9 insect cells (ATCC CRL-1711) were maintained as suspension cultures in Sf900-II insect serum free medium (ThermoFisher) at 28° C. Plaque isolates expressing GOI were amplified by infecting Sf9 cells seeded in shaker flasks at 2×106 cells/ml at a multiplicity of infection (MOI)=0.05. At 72 h post-infection, culture supernatants containing the recombinant baculoviruses were harvested, clarified by centrifugation, and stored at 4° C. Titers of recombinant baculovirus stocks were determined by agarose plaque assay in Sf9 cells.

4. GOI Protein Expression

For protein expression, Sf9 cells were infected in 200-1000 ml volume for 72 h at a cell density of 2×106 cells/ml with recombinant baculoviruses at a MOI=3. Expression of GOI protein (SEQ. ID No. 4) was determined by SDS-PAGE using 4-12% gradient polyacrylamide gels (Invitrogen) and Coomassie staining and by Western blotting using antigen-specific sera.

B. Purification of Modified S1 Spike Glycoprotein of C1.2 (SEQ. ID No. 4) from Culture Supernatant Purification of the modified S1 sequence of the spike protein of C.1.2 (SEQ ID NO. 4) from culture supernatant was carried out according to the following process:

1. Passing the clarified cell culture supernatant containing the modified S1 sequence of the spike protein of C.1.2 (6 liters) through affinity chromatography resin (100 mL Capto™ Lentil Lectin column). FIG. 1 shows the resulting solution after this step, as characterized by Akta Explorer FLPC System.

Parameters:

| | |
|---|---|
| Column Dimensions | 50 mm (d) × 5.0 cm (h) |
| Load Flow Rate | 49 mL/minute (150 cm/hr) |
| Wash Flow Rate | 25 mL/minute (75 cm/hr) |
| Elution Flow Rate | 25 mL/minute (75 cm/hr) |
| Column Equilibration | 5 cvs of Buffer A |
| Load | 4L of mFL COVID S1 6His cell culture supernatant |
| Wash | 5 cvs Buffer A11 |
| Elution | 10 cv step elution @ 100% B1 |
| Fraction Size | 50 mL |

2. Passing the resulting solution through two HisTrap™ 5 mL columns (10 mL total). 20 cv gradient to 50% B. A step elution to 100% B from 19% B to elute second product species more sharply was manually programmed.

3. Dialysis of the resulting solution.

4. Filtration of the resulting solution to produce the purified modified S1 sequence of the spike protein of C.1.2 (SEQ ID NO. 4).

The purified product can subsequently be separated in aliquots and packaged.

Example 2: Exemplary Vaccines and Immunizations

Syrian golden hamsters were immunized on day 1 and 28, with approximately 7 to 10 µg of protein in 268 to 356 µL of adjuvant. Groups of five animals were immunized subcutaneously on days 1 and 28. Serum was collected and data from IgG blots for days 0, 27, 49, and 122 bleeds are shown below. A nitrocellulose blot technique for proteins was developed and used in this study. The proteins were the spike proteins of 2019 Wuhan Hu-1, Delta, and Omicron BA.1 variants of SARS-CoV-2. These proteins were utilized to detect IgG antibodies in groups of five animals immunized with the vaccine.

Figure 2:
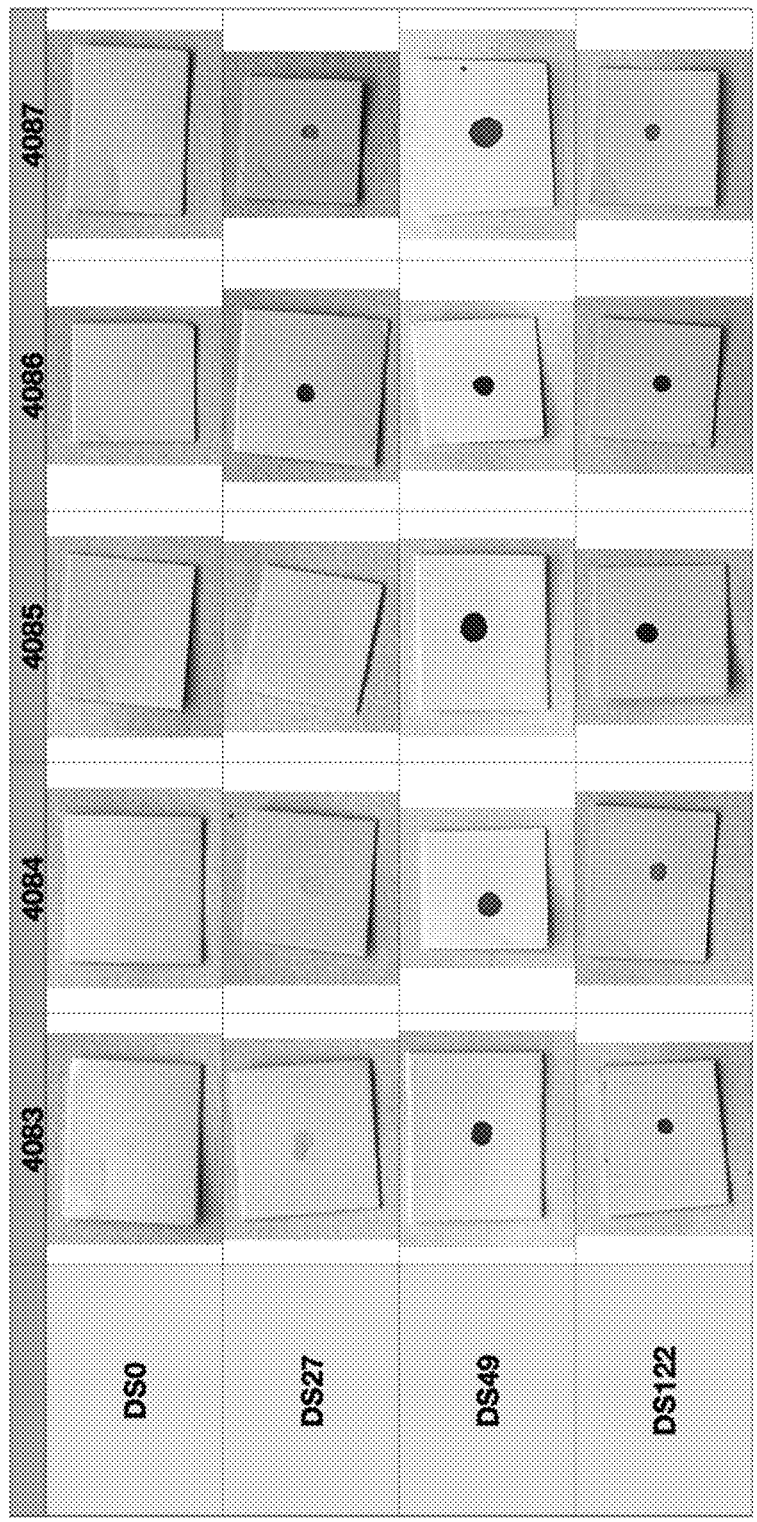
FIG. 2 depicts blot images for IgG antibodies directed against the full-length Spike protein of the 2019 Wuhan SARS-CoV-2 isolate. The animals were subcutaneously immunized with a SVE52 nonphospholipid liposome containing vitamin E and a modified S1 sequence of the C.1.2 variant of SARS-CoV-2 (SEQ. ID No. 4). Animals were bled at days 0, 27, 49, and 122. Animals were immunized on days 1 and 28. The dilution of the sera was 1:500. High antibody responses by blot were noted in all five animals at days 49 and 122.
Figure 3:
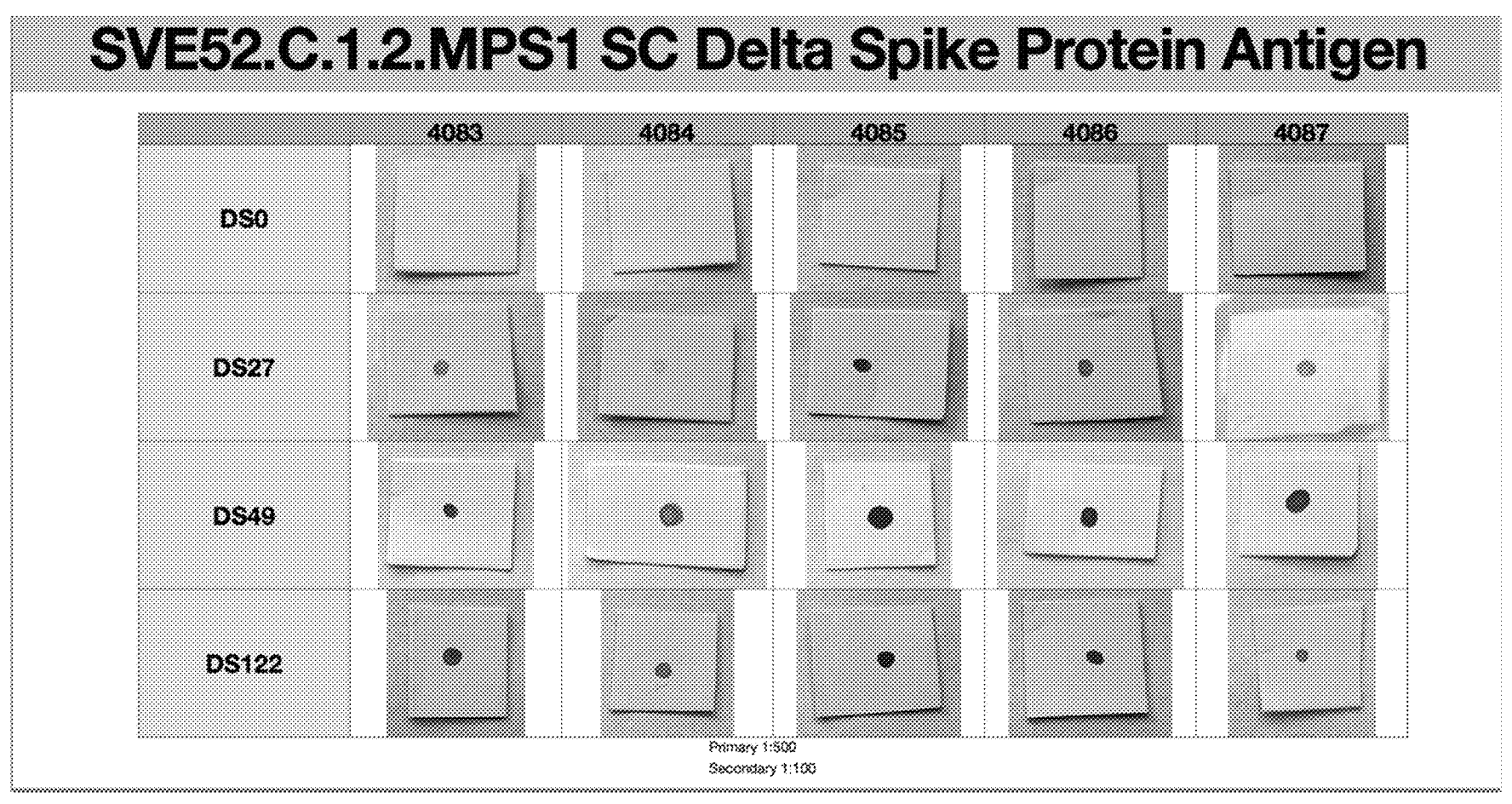
Figure 4:
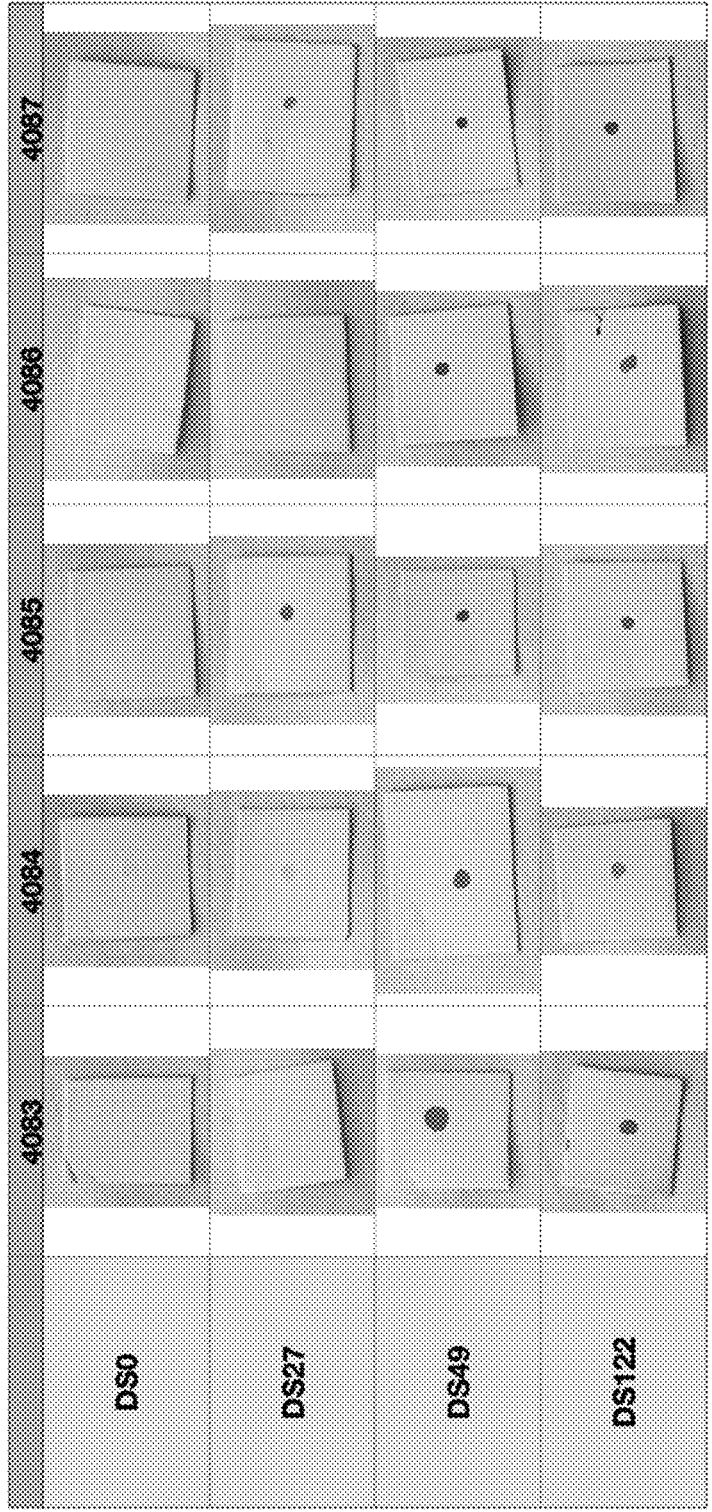
FIG. 4 depicts blot images for IgG antibodies directed against the full-length Spike protein of the SARS-CoV-2 Omicron BA.1 variant. The animals were subcutaneously immunized with a SVE52 nonphospholipid liposome containing vitamin E and a modified S1 sequence of the C.1.2 variant of SARS-CoV-2 (SEQ. ID No. 4). Animals were bled at days 0, 27, 49, and 122. Animals were immunized on days 1 and 28. The dilution of the sera was 1:500. High antibody responses by blot were noted in all five animals at days 49 and 122.
Figure 5:
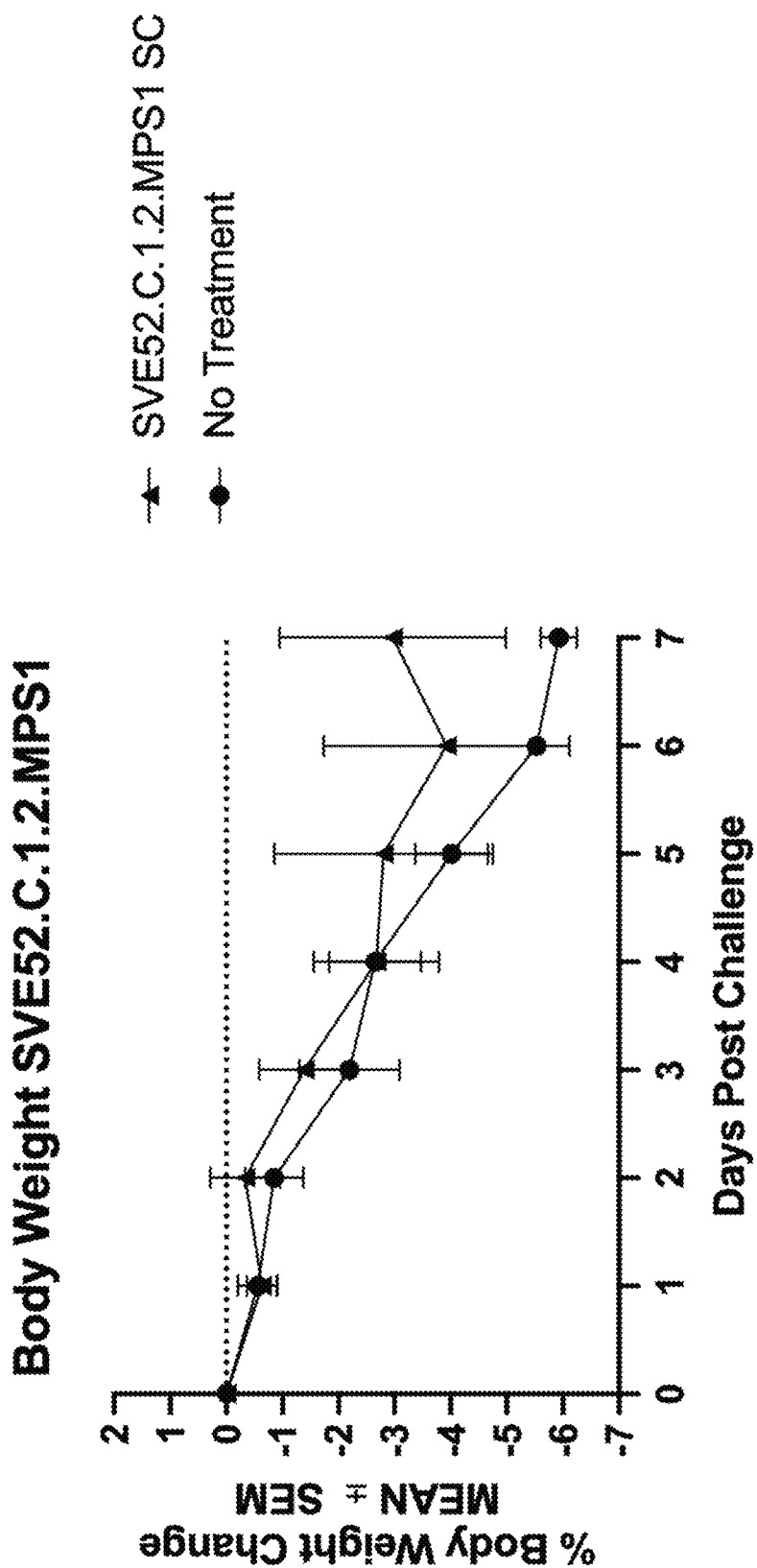
FIG. 5 depicts the percent of body weight change of the SVE52.C.1.2.MPS1 treated group and the non-treated group (n=5 per group). Body weights and clinical observations were taken during the vaccine trial, challenged on day 0 of the challenge trial with Omicron BA.1, and body weights were taken every day for 7 days post challenge. The slope of the graph between days 6 and 7 shows an increase in body weight percent change in the vaccinated group, with body weights being higher in the treated group compared to the non-treated group on day 7.
Figure 6:
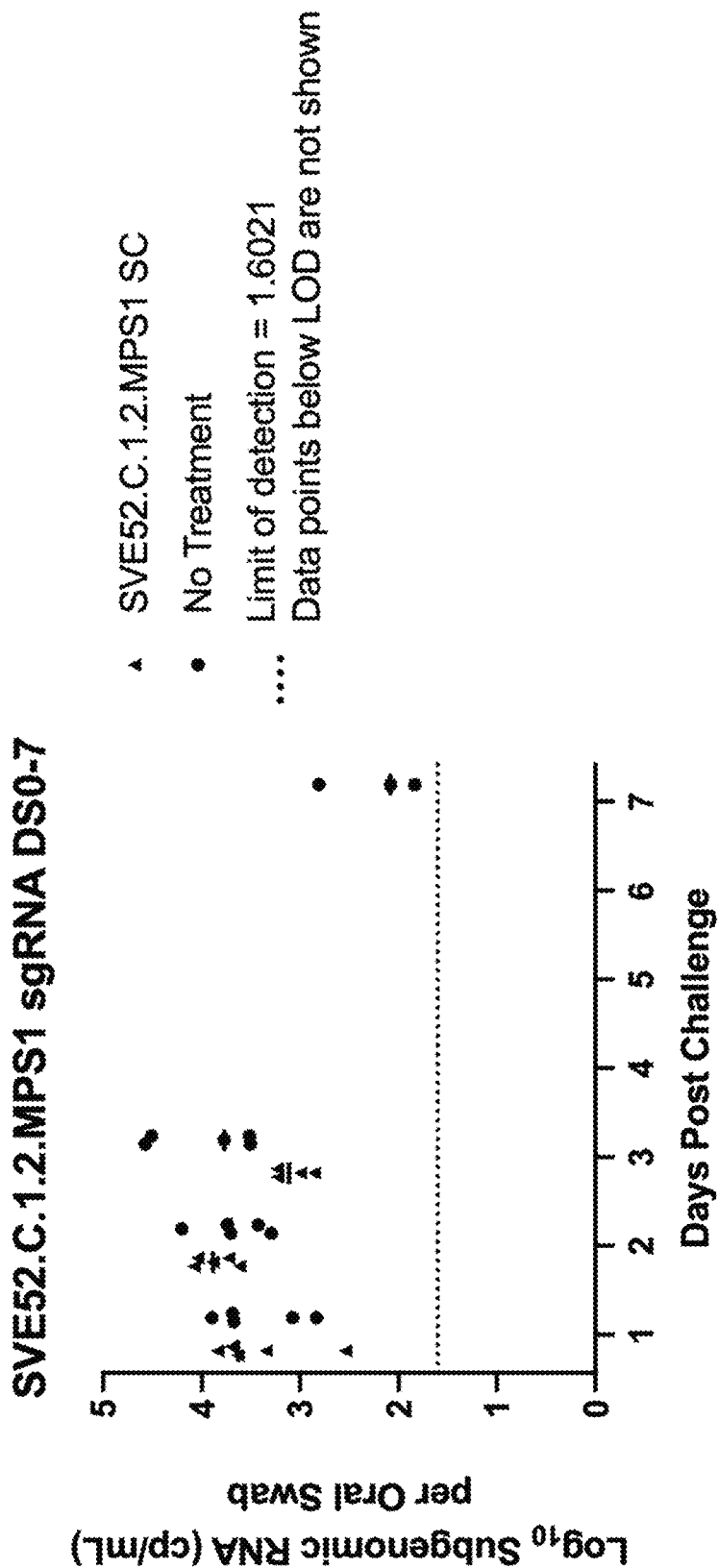
FIG. 6 depicts the viral subgenomic RNA qPCR results of the SVE52.C.1.2.MPS1 treated group and the non-treated group (n=5 per group) following a challenge with Omicron BA.1 on day 0. Oral swabs were takes at days 1, 2, 3, and 7 post infection. Data points below the limit of detection indicating no virus detected are not shown. Immunized animals begin to show a decrease in viral titer by day 3, with five out of five animals showing no detectable virus in the treated group at day 7.

All animals were immunized subcutaneously. FIGS. 2-4 show the bleed test data. Blot images show IgG antibodies directed against the spike proteins of 2019 Wuhan Hu-1, Delta, and Omicron BA.1 variants of SARS-CoV-2.

The adjuvant formulations used for the above experiments were prepared using a reciprocating syringe technique which produced 5 milliliters of adjuvanted protein vaccine. The lipid formulations were composed of polyoxyethylene-2-stearyl-ether (28.10 g), cholesterol (10.8 g), Vitamin E (5.4 g), and oleic acid (120 µl), or polyoxyethylene-2-cetyl-ether (30.01 g), cholesterol (12.80 g), Vitamin E (6.00 g), and oleic acid (125 µl). SVE are the initials for the Vitamin E-containing nonphospholipid-based liposome adjuvant.

Protein was solubilized in sterile water for injection at a concentration of 1.25 mg/mL. The lipid to diluent ratio on mixing was 1:4 on a volume basis. The final concentration of protein in the adjuvanted vaccine was approximately 7 to 10 µg of protein in 268 to 356 µL of adjuvant.

Particle sizing of the exemplary vaccines was obtained via Beckman Coulter Laser Sizer LS 13 320 XR for initial samples (T1) and also samples stored at 4-8° C. for one year. Stability is determined if the size of the particles does not exceed a 10% increase in size.

Table 3 provides particle sizing results for vaccines SVE52.C.1.2.MPS1, SC from two lots of vaccine production (Lots #021522 and #031522). Lots #021522 and #031522 sizing was done initially and one year later. 200 µL of sample was diluted into 10.0 mL dH₂O, loaded onto the device until the target quantity reached 6-8% and the size was measured. Data is reported as an average of two runs in nm and the percent change reported shows product stability with a change in size of <10% increase.

TABLE 3

Sizing 1 year SVE52.C.1.2.MPS1 Lots 021522 and 031522

| Product | Lot | Size (nm) T1 | Size (nm) T1 | Change in Size (nm) T2-T1 | % Change |
|---|---|---|---|---|---|
| SVE52.C.1.2.MPS1 SC | 021522 | 903.0 | 950.0 | 47.0 nm | 5.2% Increase |
| SVE52.C.1.2.MPS1 SC | 031522 | 1078.0 | 821.0 | 257.0 nm | 23.8% Decrease |

Table 4 provides the mean amount of adjuvanted vaccine and adjuvant administered per group for Lot #021522 (n=5).

TABLE 4

Amount of Adjuvanted Vaccine and Adjuvant Administered per Group, Lot 021522 (n = 5)

| Lot 021522 | Mean Amount of Adjuvanted Vaccine Administered per Animal (μg) | Standard Deviation | Mean Amount of Antigen Administered per Animal (μg) | Standard Deviation |
|---|---|---|---|---|
| SVE52.C.1.2.MPS1 | 356 | 45.0555213 | 9.612 | 1.216499075 |

Table 5 provides the mean amount of adjuvanted vaccine and adjuvant administered per group for Lot #031522 (n=5).

TABLE 5

Amount of Adjuvanted Vaccine and Adjuvant Administered per Group for Lot 031522 (n = 5).

| Lot 031522 | Mean Amount of Adjuvanted Vaccine Administered per Animal (μg) | Standard Deviation | Mean Amount of Antigen Administered per Animal (μg) | Standard Deviation |
|---|---|---|---|---|
| SVE52.C.1.2.MPS1 | 268 | 49.69909456 | 7.236 | 1.341875553 |

Sequence Listing

Sequence ID No. 1:
The surface glycoprotein of Severe acute respiratory syndrome coronavirus 2 variant C.1.2, accession number ULM22659.1 from the NCBI protein database.
GenBank: ULM22659.1 Identical Proteins FASTA Graphics
Go to:
LOCUS ULM22659 1270 aa linear VRL 22 Feb. 2022
DEFINITION surface glycoprotein [Severe acute respiratory syndrome coronavirus 2].
ACCESSION ULM22659 VERSION ULM22659.1
DBSOURCE accession OM773431.1
KEYWORDS
SOURCE Severe acute respiratory syndrome coronavirus 2 (SARS-CoV-2)
ORGANISM Severe acute respiratory syndrome coronavirus 2
  Viruses; Riboviria; Orthornavirae;
    Pisuviricota; Pisoniviricetes; Nidovirales; Cornidovirineae; Coronaviridae; Orthocoronavirinae; Betacoronavirus; Sarbecovirus.
REFERENCE 1 (residues 1 to 1270)
  AUTHORS Wilkinson, E., et al.
  TITLE A year of genomic surveillance reveals how the SARS-CoV-2 pandemic unfolded in Africa
  JOURNAL Science 374 (6566), 423-431 (2021)
  PUBMED 34672751
REFERENCE 2 (residues 1 to 1270)
  AUTHORS Olubayo, L. A. I., et al.
  TITLE Direct Submission
  JOURNAL Submitted (22 Feb. 2022) Department of Pathology, Faculty of Health Sciences, University of Cape Town and National Health Laboratory Service, Anzio Rd Observatory, Cape Town, Western Cape Province
Method: conceptual translation.
  Location/Qualifiers
  1 . . . 1270
  /organism="Severe acute respiratory syndrome coronavirus 2"
  /isolate="SARS-CoV-2/human/SouthAfrica/NHLS-UCT-LA-Z769/2021"
  /host="*Homo sapiens*"/db_xref="taxon:2697049"
  /country="South Africa"
  /collection_date="2021-12-01"
  /collected_by="Lancet"
Protein 1 . . . 1270 CDS
  /product="surface glycoprotein" 1 . . . 1270/gene="S"
  /coded_by="OM773431.1:21495 . . . 25307"

```
  1 mfvflvllll vssqcvnltt rtqllpaytn sftrgvyypd
    kvfrssvlhs tqdlflpffs 61 nvtwfhaihv sgtngtkrfd npvlpfndgv yfasteksni
    irgwifgttl dsktqslliv 121 nnatnvvikv cefqffndpf lgvyhknnks rmesefrvys
    sannctfeyv sqpflmdleg 181 kqgnfknlse fvfknidgyf kiyskhtpin lvrglpqgfs
    aleplvdlpi ginitrfqtl 241 lhrsyltpgd sssgwtagaa ayyvgylqpr tfllkyneng
    titdavdcal dplsetkctl 301 ksftvekgiy qtsnfrvqpt esivrfpnit nlcpfgevfn
    atrfasvyaw nrkrisncva 361 dysvlynsas fstfkcygvs ptklndlcft nvyadsfvir
    gdevrqiapg qtgkiadyny 421 klpddftgcv iawnsnnlds kvggnhnyly rlfrksnlkp
    ferdisteiy qagskpcngv 481 kgfncyfplq sygfqptygv gyqpyrvvvl sfellhapat
    vcgpkkstnl vknkcvnfnf 541 ngltgtgvlt esnkkflpfq qfgrdiadtt davrdpqtle
    ilditpcsfg gvsvitpgtn 601 tsnqvavlyq gvnctevpva ihadqltptw rvystgsnvf
    qtragcliga eyvnnsyecd 661 ipigagicas yqtqtksprr arsvasqsii aytmslgaen
    svaysnnsia ipinftisvt 721 teilpvsmtk tsvdctmyic gdstecsnll lqygsfctql
    nraltgiave qdkntqevfa
```

```
781  qvkqiyktpp  ikdfggfnfs  qilpdpskps  krsfiedllf
     nkvtladagf  ikqygdclgd 841  iaardlicaq  kfnglnvlpp  lltdemiaqy  tsalltgtit
     sgwtfgagaa  lqipfamqma 901  yrfngigvtq  nvlyenqkli  anqfnsaigk  iqdslsstas
     algklqdvvn  qnaqalntlv 961  kqlssnfgai  ssvlndilsr  ldkveaevqi  drlitgrlqs
     lqtyvtqqli  raaeirasan 1021 laatkmsecv  lgqskrvdfc  gkgyhlmsfp  qsaphgvvfl
     hvtyvpaqek  nfttapaich 1081 dgkahfpreg  vfvsngthwf  vtqrnfyepq  iittdntfvs
     gncdvvigiv  nntvydplqp 1141 eldsfkeeld  kyfknhtspd  vdlgdisgin  asvvniqkei
     drlnevaknl  neslidlqel 1201 gkyegyikwp  wyiwlgfiag  liaivmvtim  lccmtsccsc
     lkgccscgsc  ckfdeddsep 1261 vlkgvklhyt
```

Sequence ID No. 2:
Full-length Spike protein of SARS-CoV-2 variant C.1.2 collected in South Africa, July 2021, 1270 amino acids.

```
mfvflvllll  vssqcvnltt  rtqllpaytn  sftrgvyypd
kvfrssvlhs  tqdlflpffs  nvtwfhaihv  sgtngtkrfd
npvlpfndgv  yfasteksni  irgwifgttl  dsktqslliv
nnatnvvikv  cefqffndpf  lgvyhknnk   skmesefrvy
ssanncfey   vsqpflmdle  gkqgnfknls  efvfknidgy
fkiyskhtpi  nlvrglpqgf  saleplvdlp  iginitrfqt
llhrsyltpg  dsssgwtaga  aayyvgylqp  mtyilkynen
gtitdavdca  ldplsetkct  lksftvekgi  yqtsnfrvqp
tesivrfpni  tnlcpfgevf  natkfasvya  wnrkrisncv
adysvlynsa  sfstfkcygv  sptkindlcf  tnvyadsfvi
rgdevrqiap  gqtgkiadyn  yklpddftgc  viawnsnkld
skvggnhnyl  yrlfrksnlk  pferdistei  yqagstpcng
vkgfncyfpl  qsygfqptyg  vgyqpyrvvv  lsfellhapa
tvcgpkkstn  lvknkcvnfn  fngltgtgvl  tesnkkflpf
qqfgrdiadt  tdavrdpqtl  eildlitpcsf ggvsvitpgt
ntsnqvavly  qgvnctevpv  aihadqltpt  wrvystgsnv
fqtragclig  aeyvnnsyec  dipigagica  syqtqtkshr
rarsvasqsi  iaytmslgae  nsvaysnnsi  aipnnftisv
tteilpvsmt  ktsvdctmyi  cgdstecinl  llqygsfctq
lnraltgiav  eqdkntqevf  aqvkqiyktp  pikdfggfnf
sqilpdpskp  skrsfiedll  fnkvtladag  fikqygdclg
diaardlica  qkfnglnvlp  plltdemiaq  ytsalltgti
tsgwtfgaga  alqipfamqm  ayrfngigvt  qnvlyenqkl
ianqfnsaig  kiqdslssta  salgklqdvv  nqnagalntl
```

```
vkqlssnfga  issvindils  rldkveaevq  idrlitgrlq
slqtyvtqql  iraaeirasa  nlaatkmsec  vlgqskrvdf
cgkgyhlmsf  pqsaphgvvf  lhvtyvpaqe  knfttapaic
hdgkahfpre  gvfvsngthw  fvtarnfyep  qiittdntfv
sgncdvvigi  vnntvydplq  peldsfkeel  dkyfknhtsp
dvdlgdisgi  nasvvniqke  idrlnevakn  lneslidlqe
lgkyegyikw  pwyiwlgfia  gliaivmvti  mlccmtsccs
clkgccscgs  cckfdeddse  pvlkgvklhy  t
```

Sequence ID No. 3:
SARS-CoV-2 variant C.1.2 modified S1 Spike protein, amino acids 1-687

```
mfvflvllll  vssqcvnltt  rtqllpaytn  sftrgvyypd
kvfrssvlhs  tqdlflpffs  nvtwfhaihv  sgtngtkrfd
npvlpfndgv  yfasteksni  irgwifgttl  dsktqslliv
nnatnvvikv  cefqffndpf  lgvyhknnk   skmesefrvy
ssanncfey   vsqpflmdle  gkqgnfknls  efvfknidgy
fkiyskhtpi  nlvrglpqgf  saleplvdlp  iginitrfqt
llhrsyltpg  dsssgwtaga  aayyvgylqp  mtyilkynen
gtitdavdca  ldplsetkct  lksftvekgi  yqtsnfrvqp
tesivrfpni  tnlcpfgevf  natkfasvya  wnrkrisncv
adysvlynsa  sfstfkcygv  sptkindlcf  tnvyadsfvi
rgdevrqiap  gqtgkiadyn  yklpddftgc  viawnsnkld
skvggnhnyl  yrlfrksnlk  pferdistei  yqagstpong
vkgfncyfpl  qsygfqptyg  vgyqpyrvvv  lsfellhapa
tvogpkkstn  lvknkcvnfn  fngltgtgvl  tesnkkflpf
qqfgrdiadt  tdavrdpqtl  eildlitpcsf ggvsvitpgt
ntsnqvavly  qgvnctevpv  aihadqltpt  wrvystgsnv
fqtragclig  aeyvnnsyec  dipigagica  syqtqtkshr
rarsvasq
```

Sequence ID No. 4:
C.1.2 modified S1 Spike protein Construct (695 amino acids)
Final vaccine construct is 695 amino acids of the modified SARS-CoV-2 C.1.2 variant S1 spike protein with an additional amino acid His-tag. His-tag is depicted below in black bolding at the C terminus of the construct. The furin cleavage site changes are also depicted in bold.

```
MFVFLVLLLL  VSSQCVNLTT  RTQLLPAYTN  SFTRGVYYPD
KVFRSSVLHS  TQDLFLPFFS  NVTWFHAIHV  SGTNGTKRFD
NPVLPFNDGV  YFASTEKSNI  IRGWIFGTTL  DSKTQSLLIV
NNATNVVIKV  CEFQFFNDPF  LGVYHKNNKS  KMESEFRVYS
SANNCTFEYV  SQPFLMDLEG  KQGNFKNLSE  FVFKNIDGYF
KIYSKHTPIN  LVRGLPQGFS  ALEPLVDLPI  GINITRFQTL
```

```
LHRSYLTPGD SSSGWTAGAA AYYVGYLQPM TYILKYNENG

TITDAVDCAL DPLSETKCTL KSFTVEKGIY QTSNFRVQPT

ESIVRFPNIT NLCPFGEVEN ATKFASVYAW NRKRISNCVA

DYSVLYNSAS FSTFKCYGVS PTKLNDLCFT NVYADSFVIR

GDEVRQIAPG QTGKIADYNY KLPDDFTGCV IAWNSNKLDS

KVGGNHNYLY RLFRKSNLKP FERDISTEIY QAGSTPCNGV

KGFNCYFPLQ SYGFQPTYGV GYQPYRVVVL SFELLHAPAT

VCGPKKSTNL VKNKCVNFNF NGLTGTGVLT ESNKKFLPFQ

QFGRDIADTT DAVRDPQTLE ILDITPCSFG GVSVITPGTN

TSNQVAVLYQ GVNCTEVPVA IHADQLTPTW RVYSTGSNVF

QTRAGCLIGA EYVNNSYECD IPIGAGICAS YQTQTKSHGL

EVLFQGPGSHHHHHH
```

Sequence ID No. 5:
Amino acids 1228-1247 of the surface glycoprotein of SARS-CoV-2 variant C.1.2.
VMVTIMLCCMTSCCSCLKGC Sequence ID No. 6:
Keratin associated protein4-7 (KRTAP4-7) from human skin, which has sequence homology to amino acids 1228-1247 of the surface glycoprotein of SARS-CoV-2 variant C.1.2.
CCMSSCC Sequence ID No. 7:
Metallothionein 1 E (MT1E) found in human liver and other tissues (accession number AA032957), which has sequence homology to amino acids 1228-1247 of the surface glycoprotein of SARS-CoV-2 variant C.1.2.
CKTSCCSC Sequence ID No. 8:
Amino acids 1186-1205 of the surface glycoprotein of SARS-CoV-2 variant C.1.2.
LNEVAKNLNESLIDLQELGK Sequence ID No. 9:
Human Coiled-coil domain-containing protein 175 isoform X8 which is found in human brain, pituitary gland, and testis (accession number XP_011535432), which has sequence homology to amino acids 1186-1205.
KNMEEGLITLQEL Sequence ID No. 10:
Amino acids 1149-1168 of the surface glycoprotein of SARS-CoV-2 variant C.1.2.
KEELDKYFKNHTSPDVDLGD Sequence ID No. 11:
Follistatin-related protein 1 isoform X1 in human placenta (accession number XP_024309095), which has sequence homology to Amino acids 1149-1168 of the surface glycoprotein of SARS-CoV-2 variant C.1.2.
EILDKYFKN Sequence ID No. 12:
Amino acids 1010-1029 of the surface glycoprotein of SARS-CoV-2 variant C.1.2.
QQLIRAAEIRASANLAATKM Sequence ID No. 13:
Human Tetratricopeptide repeat protein 28 isoform X8 found in human tissue (accession number XP_011528323), which has sequence homology to amino acids 1010-1029 of the surface glycoprotein of SARS-CoV-2 variant C.1.2.
QQLGIAEDLKDRAAEGRASSNL Sequence ID No. 14:
Amino acids 961-980 of the surface glycoprotein of SARS-CoV-2 variant C.1.2.
TLVKQLSSNFGAISSVLNDI Sequence ID No. 15:
Human ALDH1L1 protein found in human tissue (accession number AAH27241), which has sequence homology to amino acids 961-980 of the surface glycoprotein of SARS-CoV-2 variant C.1.2.
LVKNIQLEDGKMILASNFFKGAASSVL Sequence ID No. 16:
Attractin-like protein 1 which is found in human brain (accession number XP_016871528), which has sequence homology to amino acids 961-980 of the surface glycoprotein of SARS-CoV-2 variant C.1.2.
FGAISSVLNDI Sequence ID No. 17:
Attractin-like protein 1 which is found in human brain (accession number XP_016871528), which has sequence homology to amino acids 961-980 of the surface glycoprotein of SARS-CoV-2 variant C.1.2.
AIASALIDI

SEQUENCE LISTING

```
Sequence total quantity: 17
SEQ ID NO: 1             moltype = AA  length = 1270
FEATURE                  Location/Qualifiers
source                   1..1270
                         mol_type = protein
                         organism = Severe acute respiratory syndrome-related
                         coronavirus
SEQUENCE: 1
MFVFLVLLLL VSSQCVNLTT RTQLLPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFFNDPF LGVYHKNNKS RMESEFRVYS SANNCTFEYV SQPFLMDLEG  180
KQGNFKNLSE FVFKNIDGYF KIYSKHTPIN LVRGLPQGFS ALEPLVDLPI GINITRFQTL  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGKIADYNY  420
KLPDDFTGCV IAWNSNNLDS KVGGNHNYLY RLFRKSNLKP FERDISTEIY QAGSKPCNGV  480
KGFNCYFPLQ SYGFQPTYGV GYQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSPRR ARSVASQSII AYTMSLGAEN SVAYSNNSIA IPINFTISVT  720
TEILPVSMTK TSVDCTMYIC GDSTECSNLL LQYGSFCTQL NRALTGIAVE QDKNTQEVFA  780
```

```
QVKQIYKTPP IKDFGGFNFS QILPDPSKPS KRSFIEDLLF NKVTLADAGF IKQYGDCLGD    840
IAARDLICAQ KFNGLNVLPP LLTDEMIAQY TSALLTGTIT SGWTFGAGAA LQIPFAMQMA    900
YRFNGIGVTQ NVLYENQKLI ANQFNSAIGK IQDSLSSTAS ALGKLQDVVN QNAQALNTLV    960
KQLSSNFGAI SSVLNDILSR LDKVEAEVQI DRLITGRLQS LQTYVTQQLI RAAEIRASAN   1020
LAATKMSECV LGQSKRVDFC GKGYHLMSFP QSAPHGVVFL HVTYVPAQEK NFTTAPAICH   1080
DGKAHFPREG VFVSNGTHWF VTQRNFYEPQ IITTDNTFVS GNCDVVIGIV NNTVYDPLQP   1140
ELDSFKEELD KYFKNHTSPD VDLGDISGIN ASVVNIQKEI DRLNEVAKNL NESLIDLQEL   1200
GKYEQYIKWP WYIWLGFIAG LIAIVMVTIM LCCMTSCCSC LKGCCSCGSC CKFDEDDSEP   1260
VLKGVKLHYT                                                         1270

SEQ ID NO: 2              moltype = AA   length = 1270
FEATURE                   Location/Qualifiers
source                    1..1270
                          mol_type = protein
                          organism = Severe acute respiratory syndrome-related
                            coronavirus
SEQUENCE: 2
MFVFLVLLLL VSSQCVNLTT RTQLLPAYTN SFTRGVYYPD KVFRSSVLHS TQDLFLPFFS     60
NVTWFHAIHV SGTNGTKRFD NPVLPFNDGV YFASTEKSNI IRGWIFGTTL DSKTQSLLIV    120
NNATNVVIKV CEFQFFNDPF LGVYHKNNKS KMESEFRVYS SANNCTFEYV SQPFLMDLEG    180
KQGNFKNLSE FVFKNIDGYF KIYSKHTPIN LVRGLPQGFS ALEPLVDLPI GINITRFQTL    240
LHRSYLTPGD SSSGWTAGAA AYYVGYLQPR TYILKYNENG TITDAVDCAL DPLSETKCTL    300
KSFTVEKGIY QTSNFRVQPT ESIVRFPNIT NLCPFGEVFN ATKFASVYAW NRKRISNCVA    360
DYSVLYNSAS FSTFKCYGVS PTKLNDLCFT NVYADSFVIR GDEVRQIAPG QTGKIADYNY    420
KLPDDFTGCV IAWNSNKLDS KVGGNHNYLY RLFRKSNLKP FERDISTEIY QAGSTPCNGV    480
KGFNCYFPLQ SYGFQPTYGV GYQPYRVVVL SFELLHAPAT VCGPKKSTNL VKNKCVNFNF    540
NGLTGTGVLT ESNKKFLPFQ QFGRDIADTT DAVRDPQTLE ILDITPCSFG GVSVITPGTN    600
TSNQVAVLYQ GVNCTEVPVA IHADQLTPTW RVYSTGSNVF QTRAGCLIGA EYVNNSYECD    660
IPIGAGICAS YQTQTKSHRR ARSVASQSII AYTMSLGAEN SVAYSNNSIA IPNNFTISVT    720
TEILPVSMTK TSVDCTMYIC GDSTECINLL LQYGSFCTQL NRALTGIAVE QDKNTQEVFA    780
QVKQIYKTPP IKDFGGFNFS QILPDPSKPS KRSFIEDLLF NKVTLADAGF IKQYGDCLGD    840
IAARDLICAQ KFNGLNVLPP LLTDEMIAQY TSALLTGTIT SGWTFGAGAA LQIPFAMQMA    900
YRFNGIGVTQ NVLYENQKLI ANQFNSAIGK IQDSLSSTAS ALGKLQDVVN QNAQALNTLV    960
KQLSSNFGAI SSVLNDILSR LDKVEAEVQI DRLITGRLQS LQTYVTQQLI RAAEIRASAN   1020
LAATKMSECV LGQSKRVDFC GKGYHLMSFP QSAPHGVVFL HVTYVPAQEK NFTTAPAICH   1080
DGKAHFPREG VFVSNGTHWF VTQRNFYEPQ IITTDNTFVS GNCDVVIGIV NNTVYDPLQP   1140
ELDSFKEELD KYFKNHTSPD VDLGDISGIN ASVVNIQKEI DRLNEVAKNL NESLIDLQEL   1200
GKYEQYIKWP WYIWLGFIAG LIAIVMVTIM LCCMTSCCSC LKGCCSCGSC CKFDEDDSEP   1260
VLKGVKLHYT                                                         1270

SEQ ID NO: 3              moltype = AA   length = 687
FEATURE                   Location/Qualifiers
source                    1..687
                          mol_type = protein
                          organism = synthetic construct
SEQUENCE: 3
MFVFLVLLLL VSSQCVNLTT RTQLLPAYTN SFTRGVYYPD KVFRSSVLHS TQDLFLPFFS     60
NVTWFHAIHV SGTNGTKRFD NPVLPFNDGV YFASTEKSNI IRGWIFGTTL DSKTQSLLIV    120
NNATNVVIKV CEFQFFNDPF LGVYHKNNKS KMESEFRVYS SANNCTFEYV SQPFLMDLEG    180
KQGNFKNLSE FVFKNIDGYF KIYSKHTPIN LVRGLPQGFS ALEPLVDLPI GINITRFQTL    240
LHRSYLTPGD SSSGWTAGAA AYYVGYLQPR TYILKYNENG TITDAVDCAL DPLSETKCTL    300
KSFTVEKGIY QTSNFRVQPT ESIVRFPNIT NLCPFGEVFN ATKFASVYAW NRKRISNCVA    360
DYSVLYNSAS FSTFKCYGVS PTKLNDLCFT NVYADSFVIR GDEVRQIAPG QTGKIADYNY    420
KLPDDFTGCV IAWNSNKLDS KVGGNHNYLY RLFRKSNLKP FERDISTEIY QAGSTPCNGV    480
KGFNCYFPLQ SYGFQPTYGV GYQPYRVVVL SFELLHAPAT VCGPKKSTNL VKNKCVNFNF    540
NGLTGTGVLT ESNKKFLPFQ QFGRDIADTT DAVRDPQTLE ILDITPCSFG GVSVITPGTN    600
TSNQVAVLYQ GVNCTEVPVA IHADQLTPTW RVYSTGSNVF QTRAGCLIGA EYVNNSYECD    660
IPIGAGICAS YQTQTKSHRR ARSVASQ                                       687

SEQ ID NO: 4              moltype = AA   length = 695
FEATURE                   Location/Qualifiers
source                    1..695
                          mol_type = protein
                          organism = synthetic construct
SEQUENCE: 4
MFVFLVLLLL VSSQCVNLTT RTQLLPAYTN SFTRGVYYPD KVFRSSVLHS TQDLFLPFFS     60
NVTWFHAIHV SGTNGTKRFD NPVLPFNDGV YFASTEKSNI IRGWIFGTTL DSKTQSLLIV    120
NNATNVVIKV CEFQFFNDPF LGVYHKNNKS KMESEFRVYS SANNCTFEYV SQPFLMDLEG    180
KQGNFKNLSE FVFKNIDGYF KIYSKHTPIN LVRGLPQGFS ALEPLVDLPI GINITRFQTL    240
LHRSYLTPGD SSSGWTAGAA AYYVGYLQPR TYILKYNENG TITDAVDCAL DPLSETKCTL    300
KSFTVEKGIY QTSNFRVQPT ESIVRFPNIT NLCPFGEVFN ATKFASVYAW NRKRISNCVA    360
DYSVLYNSAS FSTFKCYGVS PTKLNDLCFT NVYADSFVIR GDEVRQIAPG QTGKIADYNY    420
KLPDDFTGCV IAWNSNKLDS KVGGNHNYLY RLFRKSNLKP FERDISTEIY QAGSTPCNGV    480
KGFNCYFPLQ SYGFQPTYGV GYQPYRVVVL SFELLHAPAT VCGPKKSTNL VKNKCVNFNF    540
NGLTGTGVLT ESNKKFLPFQ QFGRDIADTT DAVRDPQTLE ILDITPCSFG GVSVITPGTN    600
TSNQVAVLYQ GVNCTEVPVA IHADQLTPTW RVYSTGSNVF QTRAGCLIGA EYVNNSYECD    660
IPIGAGICAS YQTQTKSHGL EVLFQGPGSH HHHHH                              695
```

-continued

```
SEQ ID NO: 5              moltype = AA   length = 20
FEATURE                   Location/Qualifiers
source                    1..20
                          mol_type = protein
                          organism = Severe acute respiratory syndrome-related
                           coronavirus
SEQUENCE: 5
VMVTIMLCCM TSCCSCLKGC                                                    20

SEQ ID NO: 6              moltype = AA   length = 7
FEATURE                   Location/Qualifiers
source                    1..7
                          mol_type = protein
                          organism = Homo sapiens
SEQUENCE: 6
CCMSSCC                                                                   7

SEQ ID NO: 7              moltype = AA   length = 8
FEATURE                   Location/Qualifiers
source                    1..8
                          mol_type = protein
                          organism = Homo sapiens
SEQUENCE: 7
CKTSCCSC                                                                  8

SEQ ID NO: 8              moltype = AA   length = 20
FEATURE                   Location/Qualifiers
source                    1..20
                          mol_type = protein
                          organism = Severe acute respiratory syndrome-related
                           coronavirus
SEQUENCE: 8
LNEVAKNLNE SLIDLQELGK                                                    20

SEQ ID NO: 9              moltype = AA   length = 13
FEATURE                   Location/Qualifiers
source                    1..13
                          mol_type = protein
                          organism = Homo sapiens
SEQUENCE: 9
KNMEEGLITL QEL                                                           13

SEQ ID NO: 10             moltype = AA   length = 20
FEATURE                   Location/Qualifiers
source                    1..20
                          mol_type = protein
                          organism = Severe acute respiratory syndrome-related
                           coronavirus
SEQUENCE: 10
KEELDKYFKN HTSPDVDLGD                                                    20

SEQ ID NO: 11             moltype = AA   length = 9
FEATURE                   Location/Qualifiers
source                    1..9
                          mol_type = protein
                          organism = Homo sapiens
SEQUENCE: 11
EILDKYFKN                                                                 9

SEQ ID NO: 12             moltype = AA   length = 20
FEATURE                   Location/Qualifiers
source                    1..20
                          mol_type = protein
                          organism = Severe acute respiratory syndrome-related
                           coronavirus
SEQUENCE: 12
QQLIRAAEIR ASANLAATKM                                                    20

SEQ ID NO: 13             moltype = AA   length = 22
FEATURE                   Location/Qualifiers
source                    1..22
                          mol_type = protein
                          organism = Homo sapiens
SEQUENCE: 13
QQLGIAEDLK DRAAEGRASS NL                                                 22
```

```
SEQ ID NO: 14           moltype = AA  length = 20
FEATURE                 Location/Qualifiers
source                  1..20
                        mol_type = protein
                        organism = Severe acute respiratory syndrome-related
                          coronavirus
SEQUENCE: 14
TLVKQLSSNF GAISSVLNDI                                                    20

SEQ ID NO: 15           moltype = AA  length = 27
FEATURE                 Location/Qualifiers
source                  1..27
                        mol_type = protein
                        organism = Homo sapiens
SEQUENCE: 15
LVKNIQLEDG KMILASNFFK GAASSVL                                            27

SEQ ID NO: 16           moltype = AA  length = 11
FEATURE                 Location/Qualifiers
source                  1..11
                        mol_type = protein
                        organism = Homo sapiens
SEQUENCE: 16
FGAISSVLND I                                                             11

SEQ ID NO: 17           moltype = AA  length = 9
FEATURE                 Location/Qualifiers
source                  1..9
                        mol_type = protein
                        organism = Homo sapiens
SEQUENCE: 17
AIASALIDI                                                                 9
```

We claim:

1. An adjuvanted protein vaccine comprising: a SARS-CoV-2 variant C.1.2 modified S1 Spike protein sequence and a non-phospholipid liposome, wherein the protein is encapsulated within the non-phospholipid liposome.

2. The adjuvanted protein vaccine of claim 1, wherein the one or more proteins comprise a C.1.2 modified S1 Spike protein sequence that generates IgG antibody responses for 122 days after two injections of the adjuvanted protein vaccine.

3. The adjuvanted protein vaccine of claim 1, wherein the SARS-CoV-2 variant C.1.2 modified S1 Spike protein sequence is SARS-CoV-2 variant C.1.2 modified S1 Spike protein, amino acids (amino acids 1-687) (SEQ. ID No. 3).

4. The adjuvanted protein vaccine of claim 1, wherein the SARS-CoV-2 variant C.1.2 modified S1 Spike protein sequence is the modified SARS-CoV-2 C.1.2 variant S1 spike protein with an additional amino acid His-tag (695 amino acids) (SEQ. ID No. 4).

5. The adjuvanted protein vaccine of claim 1, wherein the vaccine facilitates generation of IgG antibodies to spike proteins from multiple SARS-CoV-2 variants.

6. The adjuvanted protein vaccine of claim 1, wherein the non-phospholipid liposome comprises: one or more polyoxyethylene fatty acid ethers, one or more membrane stabilizing agents, one or more negative charge producing agents, and Vitamin E.

7. A modified spike protein sequence containing SARS-CoV-2 variant C.1.2 modified S1 Spike protein (amino acids 1-687) (SEQ. ID No. 3) or modified SARS-CoV-2 C.1.2 variant S1 spike protein with an additional amino acid His-tag (695 amino acids) (SEQ. ID No. 4).

8. The modified spike protein sequence of claim 7, wherein the sequence is SARS-CoV-2 variant C.1.2 modified S1 Spike protein, amino acids (amino acids 1-687) (SEQ. ID No. 3).

9. The modified spike protein sequence of claim 7, wherein the sequence is SARS-CoV-2 C.1.2 variant S1 spike protein with an additional amino acid His-tag (695 amino acids) (SEQ. ID No. 4).

10. A method for generating an immune response in a subject, or preventing an infection in a subject, comprising administering an adjuvanted protein vaccine according to claim 1 to a subject.

11. The method of claim 10, wherein the adjuvanted protein vaccine is administered subcutaneously or intramuscularly.

12. The method of claim 10, wherein the method generates an IgG immune response.

13. The method of claim 10, wherein the method increases the immune response to SARS-CoV-2 spike protein.

14. The method of claim 10, wherein the adjuvanted protein vaccine comprises one or more proteins that comprise a modified S1 Spike protein that generates IgG antibody responses for 122 days after two injections of the adjuvanted protein vaccine, by subcutaneous or intramuscular routes.

15. The method of claim 13, wherein the adjuvanted protein vaccine comprises SARS-CoV-2 variant C.1.2 modified S1 Spike protein, amino acids (amino acids 1-687) (SEQ. ID No. 3).

16. The method of claim 13, wherein the adjuvanted protein vaccine comprises SARS-CoV-2 C.1.2 variant S1 spike protein with an additional amino acid His-tag (695 amino acids) (SEQ. ID No. 4).

* * * * *